(12) United States Patent
Bellini et al.

(10) Patent No.: US 10,610,513 B2
(45) Date of Patent: Apr. 7, 2020

(54) BIOPHOTONIC COMPOSITIONS FOR THE TREATMENT OF OTITIS EXTERNA

(71) Applicants: KLOX TECHNOLOGIES LIMITED, Dublin (IE); Francesco Bellini, Calgary (CA); Matteo Cerquetella, Matelica (IT); Adolfo Maria Tambella, Matelica (IT); Andrea Spaterna, Matelica (IT); Nikolaos Loupis, Athens (GR); David Ohayon, Dollard-des-Ormeaux (CA); Remigio Piergallini, San Benedetto del Tronto (IT)

(72) Inventors: Francesco Bellini, Calgary (CA); Matteo Cerquetella, Matelica (IT); Adolfo Maria Tambella, Matelica (IT); Andrea Spaterna, Matelica (IT); Nikolaos Loupis, Athens (GR); David Ohayon, Dollard-des-Ormeaux (CA); Remigio Piergallini, San Benedetto del Tronto (IT)

(73) Assignee: KLOX TECHNOLOGIES LIMITED, Dublin (IE)

( * ) Notice: Subject to any disclaimer, the term of this patent is extended or adjusted under 35 U.S.C. 154(b) by 0 days.

(21) Appl. No.: 16/068,702

(22) PCT Filed: Jan. 11, 2017

(86) PCT No.: PCT/CA2017/050032
§ 371 (c)(1),
(2) Date: Jul. 9, 2018

(87) PCT Pub. No.: WO2017/120671
PCT Pub. Date: Jul. 20, 2017

(65) Prior Publication Data
US 2019/0029994 A1    Jan. 31, 2019

Related U.S. Application Data

(60) Provisional application No. 62/277,263, filed on Jan. 11, 2016.

(51) Int. Cl.
| | | |
|---|---|---|
| A61K 31/352 | (2006.01) | |
| A61K 41/00 | (2020.01) | |
| A61K 9/00 | (2006.01) | |
| A61K 9/06 | (2006.01) | |
| A61K 31/17 | (2006.01) | |
| A61K 33/40 | (2006.01) | |
| A61P 27/16 | (2006.01) | |
| A61P 31/02 | (2006.01) | |
| A61K 47/38 | (2006.01) | |
| A61K 31/4166 | (2006.01) | |
| A61K 31/7008 | (2006.01) | |
| A61K 31/715 | (2006.01) | |
| A61K 45/06 | (2006.01) | |
| A61K 47/32 | (2006.01) | |

(52) U.S. Cl.
CPC .......... *A61K 31/352* (2013.01); *A61K 9/0046* (2013.01); *A61K 9/06* (2013.01); *A61K 31/17* (2013.01); *A61K 33/40* (2013.01); *A61K 41/00* (2013.01); *A61K 45/06* (2013.01); *A61K 47/38* (2013.01); *A61P 27/16* (2018.01); *A61P 31/02* (2018.01); *A61K 31/4166* (2013.01); *A61K 31/7008* (2013.01); *A61K 31/715* (2013.01); *A61K 47/32* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 4,402,959 A | 9/1983 | Dybas et al. | |
| 4,430,381 A | 2/1984 | Harvey et al. | |
| 4,533,435 A | 8/1985 | Intili | |
| 4,625,026 A | 11/1986 | Kim | |
| 4,736,467 A | 4/1988 | Schwarze et al. | |
| 4,855,139 A | 8/1989 | Srinivasan | |
| 5,069,907 A | 12/1991 | Mixon et al. | |
| 5,091,102 A | 2/1992 | Sheridan | |
| 5,639,464 A | 6/1997 | Terry et al. | |
| 5,853,883 A | 12/1998 | Nohr et al. | |
| 5,854,147 A | 12/1998 | Nohr et al. | |
| 5,894,042 A | 4/1999 | Ferralli | |
| 5,919,554 A | 7/1999 | Watterson, III et al. | |
| 8,476,319 B2 * | 7/2013 | Scholz ................. | A61K 31/045 514/549 |

(Continued)

FOREIGN PATENT DOCUMENTS

| | | |
|---|---|---|
| CA | 2806094 A1 | 2/2012 |
| WO | 2007025244 A1 | 3/2007 |

(Continued)

OTHER PUBLICATIONS

Lee et al., "Photodynamic Therapy Using a 632 nm Diode Laser on Otitis Externa of the Dog", Journal of Veterinary clinic, 2014, 31(1), 66-69.
Street et al., "In Vitro Photodynamic Eradication of Pseudonomas aeruginosa in Planktonic and Biofilm Culture", Photochemistry and Photobiology, 2009, 85, 137-143.
Lins et al., "Enhancement of Antimicrobial Action of Photodynamic Therapy in the Presence of Hydrogen Peroxide", in "Microbial Pathogens and Strategies for Combating Them: Science, Technology and Education", Edition: Microbiology Book Series 4, Editor: A. Mendez-Vilas, 2013, pp. 367-371.

(Continued)

*Primary Examiner* — Brian J Davis
(74) *Attorney, Agent, or Firm* — BCF LLP

(57) ABSTRACT

The present disclosure describes methods and uses of biophotonic compositions which comprise at least one oxidant and at least one chromophore capable of activating the oxidant, in association with a pharmacologically acceptable carrier for the treatment of otitis externa.

20 Claims, 39 Drawing Sheets

(56) References Cited

U.S. PATENT DOCUMENTS

| | | |
|---|---|---|
| 8,945,061 B2* | 2/2015 | Branch .................. A61F 11/00 514/31 |
| 2004/0009227 A1 | 1/2004 | Yao |
| 2008/0119914 A1 | 5/2008 | Rose et al. |
| 2011/0081530 A1 | 4/2011 | Robinson et al. |

FOREIGN PATENT DOCUMENTS

| | | | |
|---|---|---|---|
| WO | 2010051636 A1 | 5/2010 | |
| WO | 2010051641 A1 | 5/2010 | |
| WO | WO 2014/036165 A1 * | 3/2014 | ............. A01N 43/42 |

OTHER PUBLICATIONS

Caccianiga et al., "Photodynamic therapy (Association diode laser/ hydrogen peroxide): Evaluation of bacterial effects on periodintipathic bacteria: An In Vitro study", European Journal of Inflammation, 2012, 10, 101-106.

Awad et al., In Vitro Photodynamic Antimicrobial Activity of Protoporphyrin IX in the Presence of Hydrogen Peroxide against *Staphylococcus aureus* and Pseudomonas aeruginosa, British Microbiology Research Journal, 4(11), 1219-1234.

Brock et al., "Use of In Vitro and In Vivo Data in the Design, Development, and Quality Control of Sustained-Release Decongestant Dosage Forms", Pharmacotherapy, vol. 14, No. 4, 1994.

Durrani et al., "Studies on Drugs Release Kinetics From Carbopol® 934P Tablets", Pharmaceutical Res. Supp. 8: S-135, 1991—abstract only.

Nuttall et al., "A pilot study to develop an objective clinical score for canine otitis externa", Veterinary Dermatology, 25(6), pp. 530-e92, 2014.

Hill et al., "The new scale proved to be an easy and repeatable method for owners to determine the severity of pruritus in their dogs", Veterinary Dermatology, 18, pp. 301-308, 2007.

Rybnicek et al., "Further validation of a pruritus severity scale for use in dogs", Veterinary Dermatology, 20, pp. 115-122, 2008.

Grono, "Studies of the microclimate of the external auditory canal in the dog", Research in Veterinary Science, 11, pp. 307-311, 1970.

Hill et al., "Pilot study of the effect of individualised homeopathy on the pruritus associated with atopic dermatitis in dogs", Veterinary Record, 164(12), pp. 364-370, 2009.

Wolfe et al., "Evaluation of a local anesthetic delivery system for the postoperative analgesic management of canine total ear canal ablation—a randomized, controlled, double-blinded study", Veterinary Anaesthesia and Analgesia, 33 (5), pp. 328-339, 2006.

Buback et al., "Comparison of three methods for relief of pain after ear canal ablation in dogs", Veterinary Surgery, 25(5), pp. 380-385, 1996.

Mittal et al., "Immunity Genes and Susceptibility to Otitis Media: A Comprehensive Review", Journal of Genetics and Genomics, 41(11), pp. 567-581, 2014.

Mittal et al., "Role of innate immunity in the pathogenesis of ottits media", International Journal of Infectious Diseases, 29, pp. 259-267, 2014.

Cole, "Anatomy and Physiology of the canine ear", Veterinary Dermatology, 20, pp. 412-421, 2009.

Cole et al., "Plasma and ear tissue concentrations of enrofloxacin and its metabolite ciprofloxacin in dogs chronic end-stage otitis externa after intravenous administration of enrofloxacin", Veterinary Dermatology, 20(1), pp. 51-59, 2009.

Santoro et al., "Cutaneous sterile pyogranuloma/granuloma syndrome in a dog", The Canadian Veterinary Journal, 49(12), pp. 1204-1207, 2008.

* cited by examiner

--PRIOR ART--

--PRIOR ART--

BIOPHOTONIC COMPOSITIONS FOR THE TREATMENT OF OTITIS EXTERNA

RELATED APPLICATIONS

This application claims priority to and benefit from U.S. Provisional Patent Application No. 62/277,263, filed Jan. 11, 2016, the disclosure of which is incorporated herein by reference in its entirety.

TECHNICAL FIELD

This description relates to the field of biophotonic compositions, methods, and uses for treating otitis externa.

BACKGROUND

Otitis externa is an inflammation or infection of the external auditory canal, the pinna (auricle), or both. The disease can be a local condition (e.g., atopic dermatitis, food hypersensitivity, parasitic diseases, or seborrhea, etc.) or part of a systemic disease (e.g., food allergy, endocrinopathies, etc.). The disease arises from primary causes, such as foreign bodies, infections, parasites, glandular hyperplasia, etc., and secondary causes, such as bacteria, chemicals, and yeast. Usually secondary causes are complicating factors from a previously existing condition that can lead to otitis externa if one or more predisposing factors are present at the same time. For instance, predisposing factors are able to alter the ventilation of the external auditory canal, thus increasing the humidity and temperature of the external auditory canal (e.g., obstructive diseases such as neoplasms, frequent baths, swimming, abundant hairs inside the external auditory canal, pendulous pinna, hypertrichlosis, etc.). The presence of predisposing factors tends to be the cause of disease persistence, and untreated otitis externa can lead to irreversible changes of the external auditory canal, such as metaplasia and ossification, and the concomitant presence of otitis media. For these reasons, chronic otitis externa is a difficult disease to manage and treat.

One of the main aspects involved in the chronicity of the disease is the presence of infections caused by bacteria resistant to different antibiotics (e.g., *Pseudomonas aeruginosa*). To manage such conditions, usually, both topical and systemic long lasting (1 to 2 months) antibiotic treatments are needed, followed by anti-inflammatory drugs. Furthermore, in an occurrence of purulent discharge, the external auditory canal has to be rinsed and cleaned with specific detergents; otherwise topical antibiotics may be ineffective. Nevertheless, even with topical antibiotics, without solving the primary cause, the condition will inevitably relapse. Different surgical procedures are possible (e.g., from lateral ear canal resection to total ear canal ablation with lateral osteotomy of the tympanic bulla), but these procedures leave a permanent aftermath.

Otitis externa is a common inflammatory disease in mammals, such as humans, dogs, and cats. For instance, swimmers are particularly prone to otitis externa due to repeated exposure to water. Additionally, otitis externa afflicts up to 10-20% of dogs visited in a first opinion veterinary clinic.

Effective treatments of otitis externa and chronic or relapsing otitis externa are needed.

SUMMARY OF DISCLOSURE

In some aspects, the present disclosure provides a method of treating otitis externa or chronic otitis externa comprising: (1) applying a biophotonic composition to a patient in need thereof, wherein the biophotonic composition comprises at least one oxidant and at least one chromophore capable of activating the oxidant; and (2) exposing said biophotonic composition to actinic light for a time sufficient for said chromophore to cause activation of said oxidant. In certain such aspects, the patient being treated is a mammal, such as a human, a feline, or a canine. In certain embodiments, the composition is applied to an auricle and/or ear canal of the patient.

In some embodiments, said biophotonic composition is exposed to actinic light for a period of less than 5 minutes, e.g., for a period of from about 1 second to about 5 minutes. In certain embodiments, said biophotonic composition is exposed to actinic light for a period of less than about 5 minutes per $cm^2$ of an area to be treated, e.g., for a period of from about 1 second to about 5 minutes per $cm^2$.

In some embodiments, the source of actinic light is positioned over an area to be treated. In certain embodiments, said actinic light is visible light having a wavelength between about 400 nm and about 700 nm.

In some embodiments, the oxidant is chosen from hydrogen peroxide, carbamide peroxide, and benzoyl peroxide, such as carbamide peroxide. In some embodiments, the oxidant is chosen from a peroxy acid and an alkali metal percarbonate. In some embodiments, the oxidant is present in an amount of from about 1% to about 10% by weight of the total composition, such as from about 3% to 9%, from about 4% to 8%, from about 5% to 7%.

In some embodiments, the composition further comprises at least one healing factor chosen from hyaluronic acid, glucosamine, and allantoin.

In some embodiments, the composition further comprises at least one gelling agent, such as glucose, modified starch, methyl cellulose, carboxymethyl cellulose, propyl cellulose, hydroxypropyl cellulose, a carbomer, alginic acid, sodium alginate, potassium alginate, ammonium alginate, calcium alginate, agar, carrageenan, locust bean gum, pectin, or gelatin.

In some embodiments, the chromophore is chosen from a xanthene derivative dye, an azo dye, a biological stain, and a carotenoid. In certain such embodiments, said xanthene derivative dye is chosen from a fluorene dye (e.g., a pyronine dye, such as pyronine Y or pyronine B, or a rhodamine dye, such as rhodamine B, rhodamine G, or rhodamine WT), a fluorone dye (e.g., fluorescein or fluorescein derivatives, such as phloxine B, rose bengal, merbromine, Eosin Y, Eosin B, or Erythrosine B, i.e., Eosin Y), or a rhodole dye. In certain such embodiments, said azo dye is chosen from methyl violet, neutral red, para red, amaranth, carmoisine, allura red AC, tartrazine, orange G, ponceau 4R, methyl red, and murexide-ammonium purpurate. In certain such embodiments, said biological stain is chosen from saffranin O, basic fuchsin, acid fuschin, 3,3' dihexylocarbocyanine iodide, carminic acid, and indocyanine green. In certain such embodiments, said carotenoid is chosen from crocetin, a-crocin (S,S-diapo-S,S-carotenoic acid), zeaxanthine, lycopene, α-carotene, β-carotene, bixin, and fucoxanthine. In certain such embodiments, said carotenoid is present in the composition as a mixture chosen from saffron red powder, annatto extract, and brown algae extract.

In some embodiments, said composition further comprises at least one chelating agent chosen from ethylenediaminetetraacetic acid (EDTA) and ethylene glycol tetraacetic acid (EGTA).

In some embodiments, the patient is treated once for one or more weeks, such as once for one week, once for two weeks, once for three weeks, once for four weeks, once for five weeks, once for six weeks. In some embodiments, the patient is treated twice for one or more weeks, such as twice for one week, twice for two weeks, twice for three weeks, twice for four weeks, twice for five weeks, twice for six weeks, twice for seven weeks.

In some aspects, the present disclosure provides for use of a biophotonic composition for the manufacture of a medicament for treating a patient afflicted with otitis externa or chronic otitis externa, wherein said composition comprises: at least one oxidant, and at least one chromophore capable of activating the oxidant; in association with a suitable carrier, such as a pharmacologically acceptable carrier. In certain such aspects, the patient is a mammal, such as a human, a feline or a canine.

In some aspects, the present disclosure provides for use of a biophotonic composition for the treatment of a patient afflicted with otitis externa or chronic externa, wherein said composition comprises: at least one oxidant, and at least one chromophore capable of activating the oxidant; in association with a suitable carrier, such as a pharmacologically acceptable carrier. In certain such aspects, the patient is a mammal, such as a human, a feline or a canine.

Definitions

Before continuing to describe the present disclosure in further detail, it is to be understood that this disclosure is not limited to specific compositions or process steps, as such may vary. It must be noted that, as used in this disclosure and the appended embodiments, the singular form "a," "an" and "the" include plural referents unless the context clearly dictates otherwise.

It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

"Biophotonic" means the generation, manipulation, detection and application of photons in a biologically relevant context. In other words, biophotonic compositions exert their physiological effects primarily due to the generation and manipulation of photons. "Biophotonic composition" is a composition as described herein that may be activated by light to produce photons for biologically relevant applications.

"Topical" means as applied to body surfaces, such as the skin, mucous membranes, vagina, oral cavity, internal surgical wound sites, and the like.

Terms "chromophore," "photoactivating agent," and "photoactivator" are used herein interchangeably. A chromophore means a compound, when contacted by light irradiation, is capable of absorbing the light. The chromophore readily undergoes photoexcitation and can then transfer its energy to other molecules or emit it as light.

The term "oxidant" is intended to mean either a compound that readily transfers oxygen atoms to and thus, oxidizes other compounds, or a substance that gains electrons in a redox chemical reaction.

The term "chelating agent" is intended to mean a compound that binds metal ions, such as iron, cobalt, copper, manganese, and chromium ions, and facilitates their solvation in solution.

The term "healing factor" is intended to mean a compound that promotes or enhances the healing or regenerative process of a tissue.

The term "active oxygen species" is intended to mean chemically-reactive molecules containing oxygen. Examples include, but are not limited to, oxygen ions and peroxides. They can be either inorganic or organic. Active oxygen species are highly reactive due to the presence of unpaired valence shell electrons. They are also referred to as "reactive oxygen," "active oxygen," or "reactive oxygen species."

Features and advantages of the subject matter hereof will become more apparent in light of the following detailed description of selected embodiments, as illustrated in the accompanying figures. As will be realized, the subject matter disclosed herein is capable of modifications in various respects, all without departing from the scope of the disclosed embodiments. Accordingly, the drawings and the description are to be regarded as illustrative in nature, and not as restrictive and the full scope of the subject matter is set forth in the embodiments.

BRIEF DESCRIPTION OF THE DRAWINGS

Further features and advantages of the present disclosure will become apparent from the following detailed description, taken in combination with the appended drawings, in which:

FIG. 8A: preparation of the therapeutic composition by mixing chromophore and urea peroxide (UP); FIG. 8B: application of the therapeutic composition locally in a canine patient.

FIG. 20A shows the erythema results; FIG. 20B shows the oedema/swelling results; FIG. 20C shows the erosion/ulceration results; and FIG. 20D shows the exudate results. FIGS. 20A-20D were plotted to show the comparison of results between Group I (Group QW), II (Group BW), and III (Group C) of the randomized controlled clinical trial.

FIGS. 22A-22B were plotted to show the comparison of results between Group I (Group QW), II (Group BW), and III (Group C) of the randomized controlled clinical trial.

FIGS. 16A-16B were plotted to show the comparison of results between Group I (Group QW), II (Group BW), and III (Group C) of the randomized controlled clinical trial.

FIGS. 24A-24C were plotted to show the comparison of results between Group I (Group QW), II (Group BW), and III (Group C) of the randomized controlled clinical trial.

FIG. 25A shows percentages of bacterial genus in Group I (Group QW) pre-treatment and after-treatment during follow-up; FIG. 25B shows percentages of bacterial genus in Group II (Group BW) pre-treatment and after-treatment during follow-up; FIG. 25C shows percentages of bacterial genus in Group III (Group C) pre-treatment and after-treatment during follow-up.

DETAILED DESCRIPTION

Figure 1:
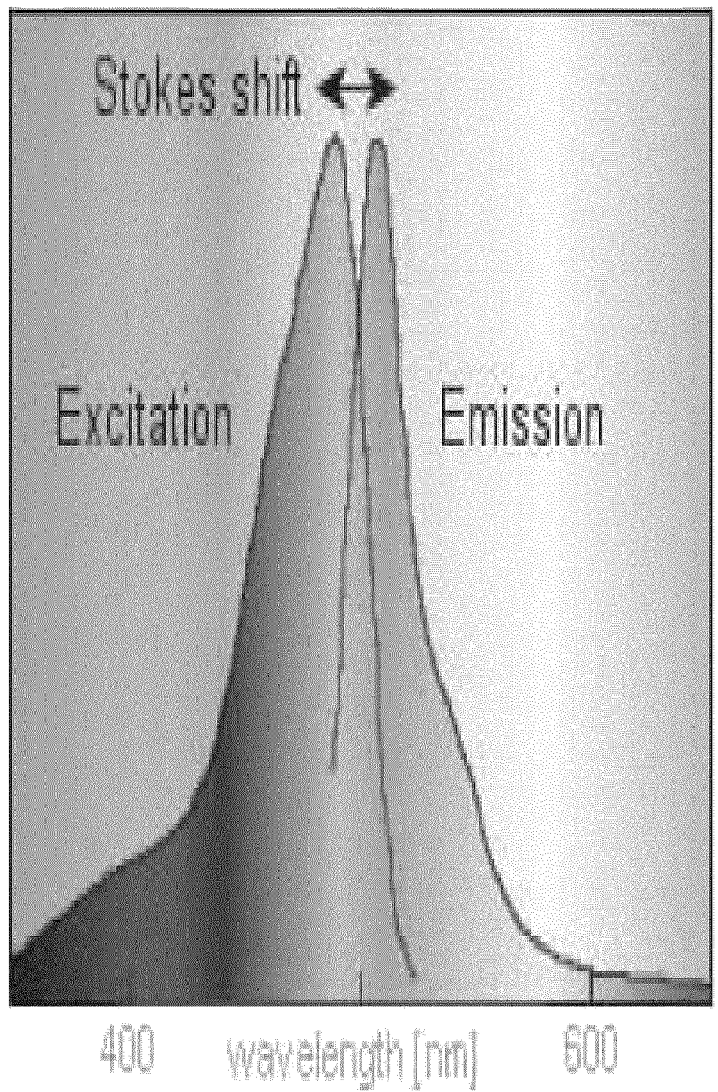
FIG. 1 illustrates the Stokes' shift.

In some aspects, the disclosure provides a method of treating otitis externa comprising: applying a biophotonic composition to a patient in need thereof, wherein the biophotonic composition comprises at least one oxidant and at least one chromophore capable of activating the oxidant; and exposing said biophotonic composition to actinic light for a time sufficient for said chromophore to cause activation of said oxidant. In certain such aspects, the patient is a mammal, such as a human, a feline, or a canine. In certain such aspects, the otitis externa is chronic otitis externa. In some embodiments, the biophotonic compositions of this disclosure are for topical use.

In some aspects, the disclosure provides for use of a biophotonic composition for the manufacture of a medicament for treating a patient afflicted with otitis externa, wherein said composition comprises: at least one oxidant, and at least one chromophore capable of activating the oxidant; in association with a pharmacologically acceptable carrier. In certain such aspects, the patient is a mammal, such as a human, a feline or a canine. In certain such aspects, the otitis externa is chronic otitis externa.

In some aspects, the disclosure provides for use of a biophotonic composition for the treatment of a patient afflicted with otitis externa, wherein said composition comprises: at least one oxidant; and at least one chromophore capable of activating the oxidant; in association with a pharmacologically acceptable carrier. In certain such aspects, the patient is a mammal, such as a human, a feline or a canine. In certain such aspects, the otitis externa is chronic otitis externa.

Biophotonic Compositions

The present disclosure provides methods and uses comprising biophotonic compositions for treating otitis externa. Biophotonic compositions are compositions that are, in a broad sense, activated by light (e.g., photons) of a specific wavelength. These compositions contain at least one exogenous chromophore (e.g., a chromophore that is not naturally present in skin or tissue of the patient being treated), which is activated by light and accelerates the dispersion of light energy, which leads to light carrying on a therapeutic effect on its own, and/or to the photochemical activation of other agents contained in the composition. The composition may comprise an agent which, when mixed with a chromophore or combination of chromophores and subsequently activated by light, can be photochemically activated which may lead to the formation of oxygen radicals, such as singlet oxygen.

In some aspects, the disclosure provides a method of treating otitis externa comprising: applying a biophotonic composition to a patient in need thereof, wherein the biophotonic composition comprises at least one oxidant and at least one chromophore capable of activating the oxidant; and exposing said biophotonic composition to actinic light for a time sufficient for said chromophore to cause activation of said oxidant.

When a chromophore absorbs a photon of a certain wavelength, it becomes excited. This is an unstable condition and the molecule tries to return to the ground state, giving away the excess energy. For some chromophores, it is favorable to emit the excess energy as light when transforming back to the ground state. This process is called fluorescence. The peak wavelength of the emitted fluorescence is shifted towards longer wavelengths compared to the absorption wavelengths ('Stokes' shift'). The emitted fluorescent energy can then be transferred to the other components of the composition or to a treatment site on to which the biophotonic composition is topically applied. Differing wavelengths of light may have different and complementary therapeutic effects on tissue. Stokes' shift is illustrated in FIG. 1.

Without being bound to theory, it is thought that fluorescent light emitted by photoactivated chromophores may have therapeutic properties due to its femto-, pico- or nano-second emission properties which may be recognized by biological cells and tissues, leading to favorable biomodulation. Furthermore, the emitted fluorescent light has a longer wavelength and hence a deeper penetration into the tissue than the activating light. Irradiating tissue with such a broad range of wavelengths, including in some embodiments the activating light which passes through the composition, may have different and complementary effects on the cells and tissues. Moreover, in some embodiments of the composition containing oxidants, micro-bubbling within the composition has been observed which may be associated with the generation of oxygen species by the photoactivated chromophores. This may have a physical impact on the tissue to which it is applied, for example by physically dislodging biofilm and debridement of necrotic tissue or providing a pressure stimulation. The biofilm can also be pre-treated with an oxygen-releasing agent to weaken the biofilm before treating with the composition of the present disclosure.

In certain embodiments, the biophotonic compositions of the present disclosure are substantially transparent/translucent and/or have high light transmittance in order to permit light dissipation into and through the composition. In this way, the area of tissue under the composition can be treated both with the fluorescent light emitted by the composition and the light irradiating the composition to activate it, which may benefit from the different therapeutic effects of light having different wavelengths.

The % transmittance of the biophotonic composition can be measured in the range of wavelengths from 250 nm to 800 nm using, for example, a Perkin-Elmer Lambda™ 9500 series UV-visible spectrophotometer. Alternatively, a Synergy™ HT spectrophotometer (BioTek Instrument, Inc.) can be used in the range of wavelengths from 380 nm to 900 nm.

Transmittance is calculated according to the following equation:

$$A_\lambda = \log_{10} \frac{I_0}{I} = \log_{10} \frac{1}{T}.$$

where A is absorbance, T is transmittance, $I_0$ is intensity of radiation before passing through material, and I is intensity of light passing through material.

The values can be normalized for thickness. As stated herein, % transmittance (translucency) is as measured for a 2 mm thick sample at a wavelength of 526 nm. It will be clear that other wavelengths can be used.

Embodiments of the biophotonic compositions of the present disclosure are for topical uses. The biophotonic composition can be in the form of a semi-solid or viscous liquid, such as a gel, or are gel-like, and which have a spreadable consistency at room temperature (e.g., about 20-25° C.), prior to illumination. By spreadable is meant that the composition can be topically applied to a treatment site at a thickness of less than about 0.5 mm, from about 0.5 mm to about 3 mm, from about 0.5 mm to about 2.5 mm, or from about 1 mm to about 2 mm. Spreadable compositions can conform to a topography of a treatment site. This can have advantages over a non-conforming material in that a better and/or more complete illumination of the treatment site can be achieved and the compositions are easy to apply and remove.

These compositions may be described based on the components making up the composition. Additionally or alternatively, the compositions of the present disclosure have functional and structural properties and these properties may also be used to define and describe the compositions. Individual components of the composition of the present disclosure are detailed below.

Oxidants

In some embodiments, the biophotonic compositions of the present disclosure comprise oxidants as a source of oxygen radicals. For instance, peroxide compounds are oxidants that contain the peroxy group (R—O—O—R), which is a chainlike structure containing two oxygen atoms, each of which is bonded to the other and a radical or some element.

In some embodiments, the biophotonic compositions of the present disclosure comprise an oxidant selected from, but not limited to, hydrogen peroxide, urea hydrogen peroxide, benzoyl peroxide, peroxy acids, or alkali metal percarbonates.

Suitable oxidants for the biophotonic compositions of the present disclosure include, but are not limited to:

Hydrogen peroxide ($H_2O_2$) is the starting material to prepare organic peroxides. $H_2O_2$ is a powerful oxidizing agent, and the unique property of hydrogen peroxide is that it breaks down into water and oxygen and does not form any persistent, toxic residual compound. Hydrogen peroxide for use in this composition can be used in a gel, for example with 6% hydrogen peroxide by weight of the total composition. A suitable range of concentration over which hydrogen peroxide can be used in a composition of the present disclosure is less than about 12% by weight of the total compositions. In some embodiments, hydrogen peroxide is present in an amount from about 0.1% to about 12%, from about 1% to about 12%, from about 3.5% to about 12%, from about 3.5% to about 6%, or from about 0.1% to about 6% by weight of the total composition.

Urea hydrogen peroxide (also known as urea peroxide, carbamide peroxide or percarbamide) is soluble in water and contains about 36% hydrogen peroxide. Carbamide peroxide for use in this composition can be used as a gel, for example with about 16% carbamide peroxide that represents about 5.6% hydrogen peroxide. A suitable range of concentration over which urea peroxide can be used in a composition of the present disclosure is less than about 36% by weight of the total composition. In some embodiments, urea peroxide is present in an amount from about 0.3% to about 36%, such as from about 3% to about 36%, from about 10% to about 36%, from about 3% to about 16%, from about 3% to about 9%, or from about 0.3% to about 16% by weight of the total composition. In some embodiments, urea peroxide is present in an amount of about 2% by weight of the total composition. In some embodiments, urea peroxide is present in an amount of about 3% by weight of the total composition. In some embodiments, urea peroxide is present in an amount of about 6% by weight of the total composition. In some embodiments, urea peroxide is present in an amount of about 8% by weight of the total composition. In some embodiments, urea peroxide is present in an amount of about 9% of the total composition. In some embodiments, urea peroxide is present in an amount of about 12% by weight of the total composition. Urea peroxide breaks down to urea and hydrogen peroxide in a slow-release fashion that can be accelerated with heat or photochemical reactions. The released urea (i.e., carbamide, $(NH_2)_2CO$) is highly soluble in water and is a powerful protein denaturant. It increases solubility of some proteins and enhances rehydration of the skin and/or mucosa.

Benzoyl peroxide consists of two benzoyl groups (benzoic acid with the H of the carboxylic acid removed) joined by a peroxide group. The released peroxide groups are effective at killing bacteria. Benzoyl peroxide also promotes skin turnover and clearing of pores. Benzoyl peroxide breaks down to benzoic acid and oxygen upon contact with skin, neither of which is toxic. A suitable range of concentration over which benzoyl peroxide can be used in the present composition is less than about 10% by weight of the total composition, such as from about 1% to 10%, from about 1% to 8%, from about 2.5% to about 5%. In some embodiments, benzoyl peroxide is present in an amount from about 1% to about 10%, or from about 1% to about 8%, or from about 2.5% to about 5% by weight of the total composition.

Suitable oxidants may also include peroxy acids and alkali metal percarbonates, but the inclusion of any other forms of peroxides (e.g., organic or inorganic peroxides) should be avoided due to their increased toxicity and their unpredictable reaction with the photodynamic energy transfer.

Chromophores/Photoactivators

In some embodiments, the biophotonic topical compositions of the present disclosure comprise one or more chromophores, which can be considered exogenous, e.g., are not naturally present in skin or tissue. When a biophotonic composition of the present disclosure is illuminated with light, the chromophore(s) are excited to a higher energy state. When the chromophore(s)' electrons return to a lower energy state, they emit photons with a lower energy level, thus causing the emission of light of a longer wavelength (Stokes' shift). In the proper environment, some of this energy release is transferred to oxygen and causes the formation of oxygen radicals, such as singlet oxygen.

Suitable chromophores for the biophotonic compositions of the disclosure can be fluorescent dyes (or stains), although other dye groups or dyes (biological and histological dyes, food colorings, carotenoids, naturally occurring fluorescent and other dyes) can also be used.

In some embodiments, the biophotonic topical composition of the present disclosure comprises a chromophore which undergoes partial or complete photobleaching upon application of light. By photobleaching is meant a photochemical destruction of the chromophore which can generally be characterized as a visual loss of color or loss of fluorescence.

In some embodiments, the chromophore absorbs at a wavelength in the range of the visible spectrum, such as at a wavelength of from about 380 to about 800 nm, such as from about 380 to about 700 nm, or from about 380 to about 600 nm. In some embodiments, the chromophore absorbs at a wavelength of from about 200 to about 800 nm, such as from about 200 to about 700 nm, from about 200 to about 600 nm, or from about 200 to about 500 nm. In some embodiments, the chromophore absorbs at a wavelength of from about 200 to about 600 nm. In some embodiments, the chromophore absorbs light at a wavelength of from about 200 to about 300 nm, from about 250 to about 350 nm, from about 300 to about 400 nm, from about 350 to about 450 nm, from about 400 to about 500 nm, from about 400 to about 600 nm, from about 450 to about 650 nm, from about 600 to about 700 nm, from about 650 to about 750 nm, or from about 700 to about 800 nm.

In some embodiments, the chromophore or combination of chromophores is present in an amount of from about 0.001 to about 40% by weight of the total composition. In some embodiments, the chromophore or combination of chromophores is present in an amount of from about 0.005 to about 2%, from about 0.01 to about 1%, from about 0.01 to about 2%, from about 0.05 to about 1%, from about 0.05 to about 2%, from about 0.1 to about 1%, from about 0.1 to about 2%, from about 1-5%, from about 2.5 to about 7.5%, from about 5 to about 10%, from about 7.5 to about 12.5%, from about 10 to about 15%, from about 12.5 to about 17.5%, from about 15 to 20%, from about 17.5 to about 22.5%, from about 20 to about 25%, from about 22.5 to about 27.5%, from about 25 to about 30%, from about 27.5 to about 32.5%, from about 30 to about 35%, from about 32.5 to about 37.5%, or from about 35 to about 40% by weight of the total composition. In some embodiments, the chromophore or combination of chromophores is present in an amount of at least about 0.2% by weight of the total composition.

In some embodiments, the chromophore or combination of chromophores is present in an amount of 0.001% to 40% by weight of the total composition. In some embodiments, the chromophore or combination of chromophores is present in an amount of from 0.005 to 2%, from 0.01 to 1%, from 0.01% to 2%, from 0.05% to 1%, from 0.05-2%, from 0.1% to 1%, from 0.1% to 2%, from 1 to 5%, from 2.5 to 7.5%, from 5 to 10%, from 7.5% to 12.5%, from 10% to 15%, from 12.5% to 17.5%, from 15% to 20%, from 17.5% to 22.5%, from 20% to 25%, from 22.5% to 27.5%, from 25% to 30%, from 27.5% to 32.5%, from 30% to 35%, from 32.5% to 37.5%, or from 35% to 40% by weight of the total composition. In some embodiments, the chromophore or combination of chromophores is present in an amount of at least 0.2% by weight of the total composition.

It will be appreciated to those skilled in the art that optical properties of a particular chromophore may vary depending on the chromophore's surrounding medium. Therefore, as used herein, a particular chromophore's absorption and/or emission wavelength (or spectrum) corresponds to the wavelengths (or spectra) measured in a biophotonic composition of the present disclosure.

In some embodiments, the biophotonic compositions disclosed herein may include at least one additional chromophore. Combining chromophores may increase photoabsorption by the combined dye molecules and enhance absorption and photo-biomodulation selectivity. This creates multiple possibilities of generating new photosensitive, and/or selective chromophores mixtures.

Figure 2:
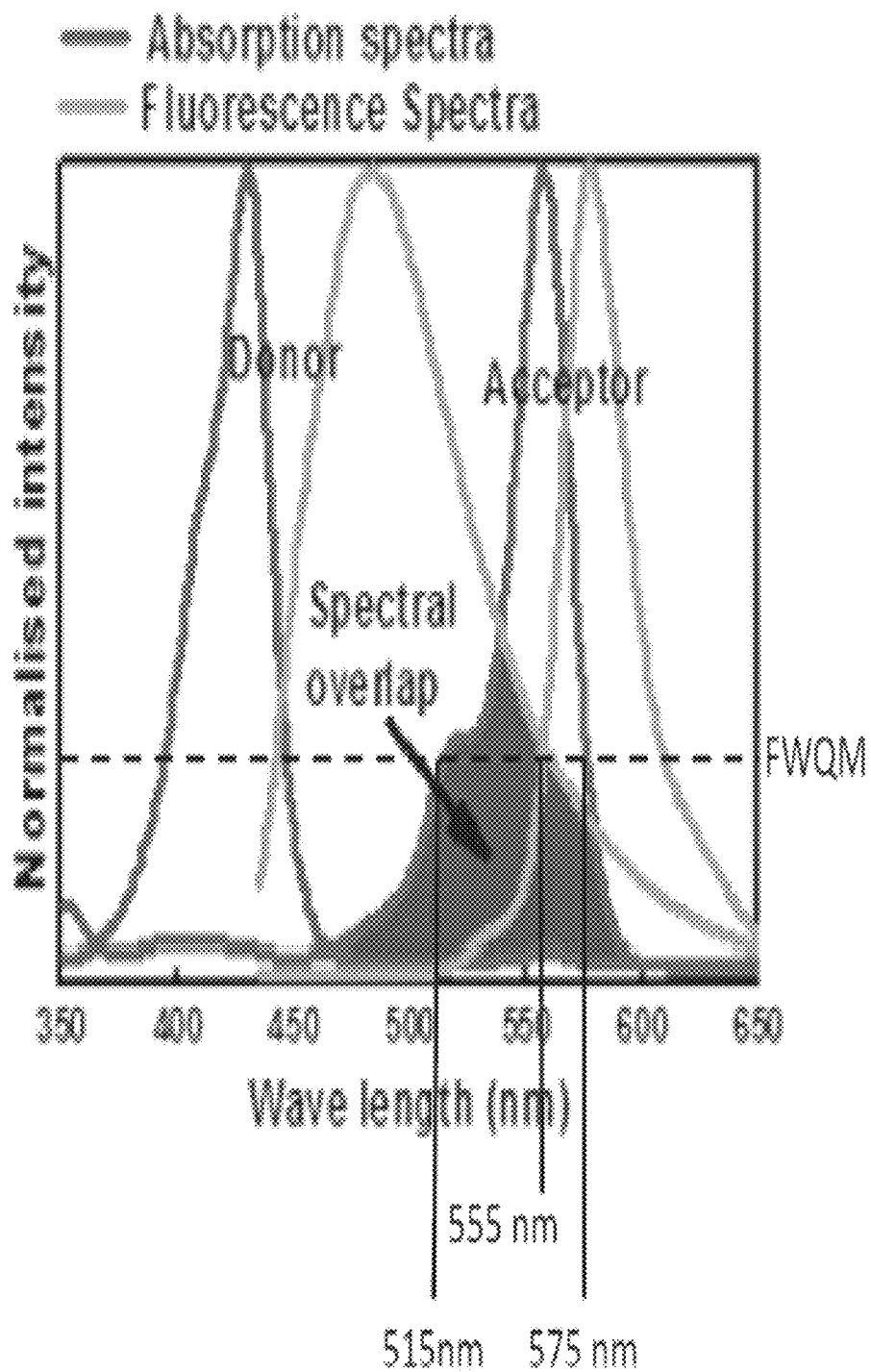
FIG. 2 illustrates the absorption and emission spectra of donor and acceptor chromophores. The spectral overlap between the absorption spectrum of the acceptor chromophore and the emission spectrum of the donor chromophore is also shown.

When such multi-chromophore compositions are illuminated with light, energy transfer can occur between the chromophores. This process, known as resonance energy transfer, is a photophysical process through which an excited 'donor' chromophore (also referred to herein as first chromophore) transfers its excitation energy to an 'acceptor' chromophore (also referred to herein as second chromophore). The efficiency and directedness of resonance energy transfer depends on the spectral features of donor and acceptor chromophores. In particular, the flow of energy between chromophores is dependent on a spectral overlap reflecting the relative positioning and shapes of the absorption and emission spectra. For energy transfer to occur the emission spectrum of the donor chromophore overlap with the absorption spectrum of the acceptor chromophore (FIG. 2).

Figure 3:
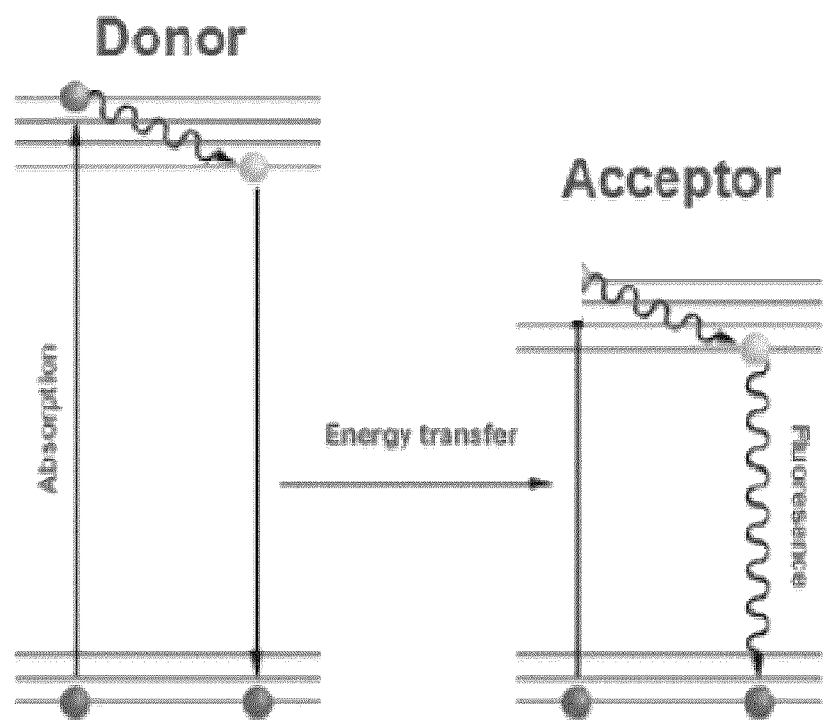
FIG. 3 is a schematic of a Jablonski diagram that illustrates the coupled transitions involved between a donor emission and acceptor absorbance.

Energy transfer manifests itself through decrease or quenching of the donor emission and a reduction of excited state lifetime accompanied also by an increase in acceptor emission intensity. FIG. 3 is a Jablonski diagram that illustrates the coupled transitions involved between a donor emission and acceptor absorbance.

To enhance the energy transfer efficiency, the donor chromophore should have good abilities to absorb photons and emit photons. Furthermore, it is thought that the more overlap there is between the donor chromophore's emission spectra and the acceptor chromophore's absorption spectra, the better a donor chromophore can transfer energy to the acceptor chromophore.

In some embodiments, the biophotonic topical composition of the present disclosure further comprises an acceptor, or a second, chromophore. In some embodiments, the donor, or first, chromophore has an emission spectrum that overlaps at least about 80%, about 70%, about 60%, about 50%, about 40%, about 30%, about 20%, or about 10% with an absorption spectrum of the second chromophore. In some embodiments, the first chromophore has an emission spectrum that overlaps at least about 20% with an absorption spectrum of the second chromophore. In some embodiments, the first chromophore has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the second chromophore.

Percentage (%) spectral overlap, as used herein, means the % overlap of a donor chromophore's emission wavelength range with an acceptor chromophore's absorption wavelength rage, measured at spectral full width quarter maximum (FWQM). For example, FIG. 2 shows the normalized absorption and emission spectra of donor and acceptor chromophores. The spectral FWQM of the acceptor chromophore's absorption spectrum is from about 60 nm (about 515 nm to about 575 nm). The overlap of the donor chromophore's spectrum with the absorption spectrum of the acceptor chromophore is about 40 nm (from 515 nm to about 555 nm). Thus, the % overlap can be calculated as 40 nm/60 nm×100=66.6%.

In some embodiments, the second chromophore absorbs at a wavelength in the range of the visible spectrum. In some embodiments, the second chromophore has an absorption wavelength that is relatively longer than that of the first chromophore within the range of about 50-250 nm, about 25-150 nm or about 10-100 nm.

As discussed above, the application of light to the compositions of the present disclosure can result in a cascade of energy transfer between the chromophores. In some embodiments, such a cascade of energy transfer provides photons that penetrate the epidermis, dermis and/or mucosa of the target tissue.

In some embodiments, the chromophore or chromophores are selected such that their emitted fluorescent light, on photoactivation, is within one or more of the green, yellow, orange, red and infrared portions of the electromagnetic spectrum, for example having a peak wavelength within the range of about 490 nm to about 800 nm. In some embodiments, the emitted fluorescent light has a power density of between 0.005 to about 10 $mW/cm^2$ or about 0.5 to about 5 $mW/cm^2$.

Suitable chromophores useful in the biophotonic topical compositions, methods, and uses of the present disclosure include, but are not limited to the following:

Xanthene Derivatives

The xanthene derivative dyes have been used and tested for a long time worldwide. They display low toxicity and increased fluorescence. The xanthene group consists of three sub-groups: a) the fluorenes; b) fluorones; and c) the rhodoles, any of which may be suitable for the biophotonic compositions, methods, and uses of the present disclosure.

The fluorenes group comprises the pyronines (e.g., pyronine Y and B) and the rhodamines (e.g., rhodamine B, G and WT). Depending on the concentration used, both pyronines and rhodamines may be toxic and their interaction with light may lead to increased toxicity. Similar effects are known to occur for the rhodole dye group.

The fluorone group comprises the fluorescein dye and the fluorescein derivatives.

Fluorescein is a fluorophore commonly used in microscopy with an absorption maximum of about 494 nm and an emission maximum of about 521 nm. The disodium salt of fluorescein is known as D&C Yellow 8. It has very high fluorescence but photodegrades quickly. In the present composition, mixtures of fluorescein with other photoactivators such as indocyanin green and/or saffron red powder will confer increased photoabsorption to these other compounds.

The eosins group comprises Eosin Y (tetrabromofluorescein, acid red 87, D&C Red 22), a chromophore with an absorption maximum of from about 514 to about 518 nm that stains the cytoplasm of cells, collagen, muscle fibers and red blood cells intensely red; and Eosin B (acid red 91, eosin scarlet, dibromo-dinitrofluorescein), with the same staining characteristics as Eosin Y. Eosin Y and Eosin B are collectively referred to as "Eosin," and use of the term "Eosin" refers to either Eosin Y, Eosin B or a mixture of both. Eosin Y, Eosin B, or a mixture of both can be used because of their sensitivity to the light spectra used: broad spectrum blue light, blue to green light and green light.

In some embodiments, the composition includes in the range of less than about 12% by weight of the total composition of at least one of Eosin B or Eosin Y or a combination thereof. In some embodiments, at least one of Eosin B or Eosin Y or a combination thereof is present from about 0.001% to about 12%, or between about 0.01% and about 1.2%, or from about 0.01% to about 0.5%, or from about 0.01% to about 0.05%, or from about 0.1% to about 0.5%, or from about 0.5% to about 0.8% by weight of the total composition. In some embodiments, at least one of Eosin B or Eosin Y or a combination thereof is present is an amount of about 0.005% by weight of the total composition. In some embodiments, at least one of Eosin B or Eosin Y or a combination thereof is present is an amount of about 0.01% by weight of the total composition. In some embodiments, at least one of Eosin B or Eosin Y or a combination thereof is present is an amount of about 0.02% by weight of the total composition. In some embodiments, at least one of Eosin B or Eosin Y or a combination thereof is present is an amount of about 0.05% by weight of the total composition. In some embodiments, at least one of Eosin B or Eosin Y or a combination thereof is present is an amount of about 0.1% by weight of the total composition. In some embodiments, at least one of Eosin B or Eosin Y or a combination thereof is present is an amount of about 0.2% by weight of the total composition. In some embodiments, at least one of Eosin B or Eosin Y or a combination thereof is present is an amount of at least about 0.2% by weight of the total composition but less than about 1.2% by weight of the total composition. In some embodiments, at least one of Eosin B or Eosin Y or a combination thereof is present is an amount of at least about 0.01% by weight of the total composition but less than about 12% by weight of the total composition.

In some embodiments, the composition includes in the range of less than 12% by weight of the total composition of at least one of Eosin B or Eosin Y or a combination thereof. In some embodiments, at least one of Eosin B or Eosin Y or a combination thereof is present from 0.001% to 12%, or from 0.01% to 1.2%, or from 0.01% to 0.5%, or from 0.1% to 0.5%, or from 0.5% to 0.8%, or from 0.01% to 0.05%, by weight of the total composition. In some embodiments, at least one of Eosin B or Eosin Y or a combination thereof is present is an amount of 0.005% by weight of the total composition. In some embodiments, at least one of Eosin B or Eosin Y or a combination thereof is present is an amount of 0.01% by weight of the total composition. In some embodiments, at least one of Eosin B or Eosin Y or a combination thereof is present is an amount of 0.02% by weight of the total composition. In some embodiments, at least one of Eosin B or Eosin Y or a combination thereof is present is an amount of 0.05% by weight of the total composition. In some embodiments, at least one of Eosin B or Eosin Y or a combination thereof is present is an amount of 0.1% by weight of the total composition. In some embodiments, at least one of Eosin B or Eosin Y or a combination thereof is present is an amount of 0.2% by weight of the total composition. In some embodiments, at least one of Eosin B or Eosin Y or a combination thereof is present is an amount of at least 0.2% by weight of the total composition but less than 1.2% by weight of the total composition. In some embodiments, at least one of Eosin B or Eosin Y or a combination thereof is present is an amount of at least 0.01% by weight of the total composition but less than 12% by weight of the total composition.

Phloxine B (2,4,5,7 tetrabromo 4,5,6,7,tetrachlorofluorescein, D&C Red 28, acid red 92) is a red dye derivative of fluorescein which is used for disinfection and detoxification of waste water through photooxidation. It has an absorption maximum of 535-548 nm. It is also used as an intermediate for making photosensitive dyes and drugs.

Erythrosine B, or simply Erythrosine or Erythrosin (acid red 51, tetraiodofluorescein) is a cherry-pink, coal-based fluorine food dye used as a biological stain, and a biofilm and dental plaque disclosing agent, with a maximum absorbance of 524-530 nm in aqueous solution. It is subject to photodegradation. Erythrosine is also used in some embodiments due to its photosensitivity to the light spectra used and its ability to stain biofilms. In embodiments, the composition includes in the range of less than about 2% by weight Erythrosine B. In some embodiments, Erythrosine B is present in an amount from about 0.005 to about 2%, or from about 0.005% to about 1%, or about 0.01% to about 1% by weight of the total composition. In some embodiments, Erythrosine B is present in an amount of about 0.005% and about 0.15% by weight of the total composition.

Rose Bengal (4,5,6,7 tetrachloro 2,4,5,7 tetraiodofluorescein, acid red 94) is a bright bluish-pink fluorescein derivative with an absorption maximum of 544-549 nm, that has been used as a dye, biological stain and diagnostic aid. Rose Bengal is also used in synthetic chemistry to generate singlet oxygen from triplet oxygen.

Merbromine (mercurochrome) is an organo-mercuric disodium salt of fluorescein with an absorption maximum of 508 nm. It is used as an antiseptic.

Azo Dyes

The azo (or diazo-) dyes share the N—N group, called azo the group. They are used mainly in analytical chemistry or as food colorings and are not fluorescent. Suitable azo dyes for the compositions, methods, and uses of the disclosure include: Methyl violet, neutral red, para red (pigment red 1), amaranth (Azorubine S), Carmoisine (azorubine, food red 3, acid red 14), allura red AC (FD&C 40), tartrazine (FD&C Yellow 5), orange G (acid orange 10), Ponceau 4R (food red 7), methyl red (acid red 2), and murexide-ammonium purpurate.

Biological Stains

Dye molecules commonly used in staining protocols for biological materials can also be used as photoactivators for the compositions, methods, and uses of the disclosure. Suitable biological stains include, but not limited to:

Saffranin (Saffranin 0, basic red 2) is an azo-dye and is used in histology and cytology. It is a classic counter stain in a Gram stain protocol.

Fuchsin (basic or acid) (rosaniline hydrochloride) is a magenta biological dye that can stain bacteria and has been used as an antiseptic. It has an absorption maximum of 540-555 nm.

3,3'-dihexylocarbocyanine iodide (DiOC6) is a fluorescent dye used for staining the endoplasmic reticulum, vesicle membranes and mitochondria of cells. It shows photodynamic toxicity; when exposed to blue light, has a green fluorescence.

Carminic acid (acid red 4, natural red 4) is a red glucosidal hydroxyanthrapurin naturally obtained from cochineal insects.

Indocyanin green (ICG) is used as a diagnostic aid for blood volume determination, cardiac output, or hepatic function. ICG binds strongly to red blood cells and when used in mixture with fluorescein, it increases the absorption of blue to green light.

Carotenoids

Carotenoid dyes are also photoactivators that are useful in the compositions, methods, and uses of the disclosure.

Saffron red powder is a natural carotenoid-containing compound. Saffron is a spice derived from crocus sativus. It is characterized by a bitter taste and iodoform or hay-like fragrance; these are caused by the compounds picrocrocin and saffranal. It also contains the carotenoid dye crocin that gives its characteristic yellow-red color.

Saffron contains more than 150 different compounds, many of which are carotenoids: mangicrocin, reaxanthine, lycopene, and various α and β-carotenes, which show good absorption of light and beneficial biological activity. Also saffron can act as both a photon-transfer agent and a healing factor. Saffron color is primarily the result of a-crocin (8,8 diapo-8,8-carotenoid acid). Dry saffron red powder is highly sensitive to fluctuating pH levels and rapidly breaks down chemically in the presence of light and oxidizing agents. It is more resistant to heat. Data show that saffron has anti-carcinogenic, immunomodulating and antioxidant properties. For absorbance, the crocin specific photon wavelength is 440 nm (blue light). It has a deep red colour and forms crystals with a melting point of 186° C. When dissolved in water, it forms an orange solution.

Crocetin, another compound of saffron, was found to express an antilipidemic action and promote oxygen penetration in different tissues. More specifically, an increased oxygenation of the endothelial cells of the capillaries was observed. Additionally, an increase of the oxygenation of muscles and cerebral cortex was observed and led to an improved survival rate in laboratory animals with induced hemorrhagic shock or emphysema.

Anatto, a spice, contains as main constituent (70-80%) the carotenoid bixin which displays relevant antioxidative properties. β-carotene, also displays suitable characteristics.

Fucoxanthine is a constituent of brown algae with a pronounced ability for photosensitization of redox reactions.

Chlorophyll Dyes

Exemplary chlorophyll dyes that are useful in the compositions, methods, and uses of the disclosure, include but are not limited to chlorophyll a, chlorophyll b, oil soluble chlorophyll, bacteriochlorophyll a, bacteriochlorophyll b, bacteriochlorophyll c, bacteriochlorophyll d, protochlorophyll, protochlorophyll a, amphiphilic chlorophyll derivative 1, and amphiphilic chlorophyll derivative 2.

In some aspects of the disclosure, the one or more chromophores of the biophotonic composition disclosed herein can be independently selected from any of Acid black 1, Acid blue 22, Acid blue 93, Acid fuchsin, Acid green, Acid green 1, Acid green 5, Acid magenta, Acid orange 10, Acid red 26. Acid red 29, Acid red 44, Acid red 51, Acid red 66, Acid red 87, Acid red 91, Acid red 92, Acid red 94, Acid red 101, Acid red 103, Acid roseine, Acid rubin, Acid violet 19, Acid yellow 1, Acid yellow 9, Acid yellow 23, Acid yellow 24, Acid yellow 36, Acid yellow 73, Acid yellow S, Acridine orange, Acriflavine, Alcian blue, Alcian yellow, Alcohol soluble eosin, Alizarin, Alizarin blue 2RC, Alizarin carmine, Alizarin cyanin BBS, Alizarol cyanin R, Alizarin red S, Alizarin purpurin, Aluminon, Amido black 10B, Amidoschwarz, Aniline blue WS, Anthracene blue SWR, Auramine O, Azocannine B, Azocarmine G, Azoic diazo 5, Azoic diazo 48, Azure A, Azure B, Azure C, Basic blue 8, Basic blue 9, Basic blue 12, Basic blue 15, Basic blue 17, Basic blue 20, Basic blue 26, Basic brown 1, Basic fuchsin, Basic green 4, Basic orange 14, Basic red 2 (Saffranin O), Basic red 5, Basic red 9, Basic violet 2, Basic violet 3, Basic violet 4, Basic violet 10, Basic violet 14, Basic yellow 1, Basic yellow 2, Biebrich scarlet, Bismarck brown Y, Brilliant crystal scarlet 6R, Calcium red, Carmine, Carminic acid (acid red 4), Celestine blue B, China blue, Cochineal, Celestine blue, Chrome violet CG, Chromotrope 2R, Chromoxane cyanin R, Congo corinth, Congo red, Cotton blue, Cotton red, Croceine scarlet, Crocin, Crystal ponceau 6R, Crystal violet, Dahlia, Diamond green B, DiOC6, Direct blue 14, Direct blue 58, Direct red, Direct red 10, Direct red 28, Direct red 80, Direct yellow 7, Eosin B, Eosin Bluish, Eosin, Eosin Y, Eosin yellowish, Eosinol, Erie garnet B, Eriochrome cyanin R, Erythrosin B, Ethyl eosin, Ethyl green, Ethyl violet, Evans blue, Fast blue B, Fast green FCF, Fast red B, Fast yellow, Fluorescein, Food green 3, Gallein, Gallamine blue, Gallocyanin, Gentian violet, Haematein, Haematine, Haematoxylin, Helio fast rubin BBL, Helvetia blue, Hematein, Hematine, Hematoxylin, Hoffman's violet, Imperial red, Indocyanin green, Ingrain blue, Ingrain blue 1, Ingrain yellow 1, INT, Kermes, Kermesic acid, Kernechtrot, Lac, Laccaic acid, Lauth's violet, Light green, Lissamine green SF, Luxol fast blue, Magenta 0, Magenta I, Magenta II, Magenta III, Malachite green, Manchester brown, Martius yellow, Merbromin, Mercurochrome, Metanil yellow, Methylene azure A, Methylene azure B, Methylene azure C, Methylene blue, Methyl blue, Methyl green, Methyl violet, Methyl violet 2B, Methyl violet 10B, Mordant blue 3, Mordant blue 10, Mordant blue 14, Mordant blue 23, Mordant blue 32, Mordant blue 45, Mordant red 3, Mordant red 11, Mordant violet 25, Mordant violet 39 Naphthol blue black, Naphthol green B, Naphthol yellow S, Natural black 1, Natural red, Natural red 3, Natural red 4, Natural red 8, Natural red 16, Natural red 25, Natural red 28, Natural yellow 6, NBT, Neutral red, New fuchsin, Niagara blue 3B, Night blue, Nile blue, Nile blue A, Nile blue oxazone, Nile blue sulphate, Nile red, Nitro BT, Nitro blue tetrazolium, Nuclear fast red, Oil red O, Orange G, Orcein, Pararosanilin, Phloxine B, phycobilins, Phycocyanins, Phycoerythrins. Phycoerythrincyanin (PEC), Phthalocyanines, Picric acid, Ponceau 2R, Ponceau 6R, Ponceau B, Ponceau de Xylidine, Ponceau S, Primula, Purpurin, Pyronin B, Pyronin G, Pyronin Y, Rhodamine B, Rosanilin, Rose bengal, Saffron, Safranin O, Scarlet R, Scarlet red, Scharlach R, Shellac, Sirius red F3B, Solochrome cyanin R, Soluble blue, Solvent black 3, Solvent blue 38, Solvent red 23, Solvent red 24, Solvent red 27, Solvent red 45, Solvent yellow 94, Spirit soluble eosin, Sudan III, Sudan IV, Sudan black B, Sulfur yellow S, Swiss blue, Tartrazine, Thioflavine S, Thioflavine T, Thionin, Toluidine blue, Toluyline red, Tropaeolin G, Trypaflavine, Trypan blue, Uranin, Victoria blue 4R, Victoria blue B, Victoria green B, Water blue I, Water soluble eosin, Xylidine ponceau, or Yellowish eosin.

Chromophores can be selected, for example, on their emission wavelength properties in the case of fluorophores, on the basis of their energy transfer potential, their ability to generate reactive oxygen species, or their antimicrobial effect.

In some embodiments, the biophotonic compositions of this disclosure comprises Eosin Y as a first chromophore. In some embodiments, the composition comprises Eosin Y as a first chromophore and any one or more of Rose Bengal, Erythrosin, Phloxine B as a second chromophore. It is believed that these combinations have a synergistic effect as Eosin Y can transfer energy to Rose Bengal, Erythrosin or Phloxine B when activated. This transferred energy is then emitted as fluorescence or by production of reactive oxygen species. This absorbed and re-emitted light is thought to be transmitted throughout the composition, and also to be transmitted into the site of treatment.

In some embodiments, the biophotonic compositions of this disclosure comprise the following synergistic combinations: Eosin Y and Fluorescein; Fluorescein and Rose Bengal; Erythrosine in combination with one or more of Eosin Y, Rose Bengal or Fluorescein; or Phloxine B in combination with one or more of Eosin Y, Rose Bengal, Fluorescein and Erythrosine. Other synergistic chromophore combinations may also be suitable for the biophotonic compositions of this disclosure.

By means of synergistic effects of the chromophore combinations in the composition, chromophores which cannot normally be activated by an activating light (such as a blue light from an LED) can be activated through energy transfer from chromophores which are activated by the activating light. In this way, the different properties of photoactivated chromophores can be harnessed and tailored according to the cosmetic or the medical therapy required.

For example, Rose Bengal can generate a high yield of singlet oxygen when photoactivated in the presence of molecular oxygen, however, it has a low quantum yield in terms of emitted fluorescent light. Rose Bengal has a peak absorption at approximately 540 nm; so it is normally activated by green light. Eosin Y has a high quantum yield and can be activated by blue light. By combining Rose Bengal with Eosin Y, one obtains a composition which can emit therapeutic fluorescent light and generate singlet oxygen when activated by blue light. In this case, the blue light photoactivates Eosin Y, which transfers some of its energy to Rose Bengal and emits some energy as fluorescence.

Chromophore combinations can also have a synergistic effect in terms of their photoactivated state. In some embodiments, two chromophores may be used, one of which emits fluorescent light when activated in the blue and green range, and the other which emits fluorescent light in the red, orange and yellow range, thereby complementing each other and irradiating the target tissue with a broad wavelength of light having different depths of penetration into target tissue and different therapeutic effects.

Healing Factors

According to some embodiments, the biophotonic compositions of the present disclosure may further comprise one or more healing factors. Healing factors include compounds that promote or enhance the healing or regenerative process of the tissues on the application site of the composition. During the photoactivation of the composition, there is an increase of the absorption of molecules at the treatment site. An augmentation in the blood flow at the site of treatment is observed for an extended period of time. An increase in the lymphatic drainage and a possible change in the osmotic equilibrium due to the dynamic interaction of the free radical cascades can be enhanced or even fortified with the inclusion of healing factors. In some embodiments, the biophotonic compositions of the present disclosure comprises one or more healing factors selected from, but not limited to, hyaluronic acid, glucosamine, allantoin, or saffron.

Suitable healing factors for the biophotonic compositions, methods and uses of the present disclosure include, but are not limited to:

Hyaluronic acid (hyaluronan or hyaluronate) is a non-sulfated glycosaminoglycan, distributed widely throughout connective, epithelial and neural tissues. It is one of the primary components of the extracellular matrix, and contributes significantly to cell proliferation and migration. Hyaluronan is a major component of the skin, where it is involved in tissue repair. While it is abundant in extracellular matrices, it contributes to tissue hydrodynamics, movement and proliferation of cells and participates in a wide number of cell surface receptor interactions, notably those including primary receptor CD44. The hyaluronidase enzymes degrade hyaluronan and there are at least seven types of hyaluronidase-like enzymes in humans, several of which are tumor suppressors. The degradation products of hyaluronic acid, the oligosaccharides and the very-low molecular weight hyaluronic acid, exhibit pro-angiogenic properties. In addition, recent studies show that hyaluronan fragments, but not the native high molecular mass of hyaluronan, can induce inflammatory responses in macrophages and dendritic cells in tissue injury. Hyaluronic acid is well suited to biological applications targeting the skin. Due to its high biocompatibility, it is used to stimulate tissue regeneration. Current studies evidenced hyaluronic acid appearing in the early stages of healing to physically create room for white blood cells that mediate the immune response. It is used in the synthesis of biological scaffolds for wound healing applications and in wrinkle treatment. In certain embodiments, the composition includes hyaluronic acid in the range of less than about 2% by weight of the total composition hyaluronic acid. In some embodiments, hyaluronic acid is present in an amount from about 0.001% to about 2%, or from about 0.002% to about 2%, or from about 0.002% to about 1% by weight of the total composition.

Glucosamine is one of the most abundant monosaccharides in human tissues and a precursor in the biological synthesis of glycosylated proteins and lipids. It is commonly used in the treatment of osteoarthritis. The common form of glucosamine used is its sulfate salt. Glucosamine shows a number of effects, including anti-inflammatory activity, stimulation of the synthesis of proteoglycans and the synthesis of proteolytic enzymes. A suitable range of concentration over which glucosamine can be used in the present composition is from less than about 5% by weight of the total composition. In some embodiments, glucosamine is present in an amount from about 0.0001% to about 5%, or from about 0.0001% to about 3%, or from about 0.001% to about 3%, or from about 0.001% to about 1%, or from about 0.01% to about 1%, or from about 1% to about 3% by weight of the total composition.

Allantoin is a diureide of glyosilic acid. It has keratolytic effect, increases the water content of the extracellular matrix, enhances the desquamation of the upper layers of dead (apoptotic) skin cells, and promotes skin proliferation and wound healing. In certain embodiments, the composition includes in the range of less than about 1% by weight of the total composition allantoin. In some embodiments, allantoin is present in an amount of from about 0.001% to about 1%, or from about 0.002% to about 1%, or from about 0.02% to about 1%, or from about 0.02% to about 0.5% by weight of the total composition.

Saffron can act as both a photon-transfer agent and a healing factor.

Chelating Agents

In some embodiments, the biophotonic compositions of the present disclosure may further comprise one or more chelating factors. Chelating agents can be included to promote smear layer removal in closed pockets and difficult to reach lesions. Chelating agents act as a metal ion quencher and as a buffer. In some embodiments, the biophotonic compositions of the present disclosure comprise a chelating factor selected from, but not limited to, ethylenediaminotetraacetic acid (EDTA) or ethylene glycol tetraacetic acid (EGTA.

Suitable chelating agents for the biophotonic compositions, methods and uses of this disclosure include, but are not limited to:

Ethylenediaminotetraacetic Acid (EDTA)

Ethylenediaminotetraacetic acid (EDTA) is an amino acid and is used to sequester di- and trivalent metal ions. EDTA binds to metals via four carboxylate and two amine groups. EDTA forms especially strong complexes with Mn(III), Fe(III), Cu(III), Co(III). It is used to buffer solutions.

Ethylene Glycol Tetraacetic Acid (EGTA)

Ethylene glycol tetraacetic acid (EGTA) is related to EDTA, but with a much higher affinity for calcium than magnesium ions. It is useful for making buffer solutions that resemble the environment inside living cells.

Gelling Agents

In some embodiments, the biophotonic compositions of the present disclosure may further comprise one or more gelling agents. The gelling agent may be an agent capable of forming a cross-linked matrix, including physical and/or chemical cross-links. The gelling agent can be biocompatible, and may be biodegradable. In some embodiments, the gelling agent is able to form a hydrogel or a hydrocolloid. An appropriate gelling agent is one that can form a viscous liquid or a semisolid. In some embodiments, the gelling agent and/or the composition has appropriate light transmission properties. It is also important to select a gelling agent which will allow biophotonic activity of the chromophore (s). For example, some chromophores require a hydrated environment in order to fluoresce. The gelling agent may be able to form a gel by itself or in combination with other ingredients such as water or another gelling agent, or when applied to a treatment site, or when illuminated with light.

The gelling agent according to various embodiments of the present disclosure may include, but not be limited to, polyalkylene oxides, particularly polyethylene glycol and poly(ethylene oxide)-poly(propylene oxide) copolymers, including block and random copolymers; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxy-ethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly(hydroxyethylmethacrylate), poly(hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly (acrylamides) such as polyacrylamide per se, poly(methacrylamide), poly(dimethylacrylamide), and poly(N-isopropyl-acrylamide); poly(olefinic alcohol)s such as poly(vinyl alcohol); poly(N-vinyl lactams) such as poly(vinyl pyrrolidone), poly(N-vinyl caprolactam), and copolymers thereof, polyoxazolines, including poly(methyloxazoline) and poly (ethyloxazoline); silicones, polyvinyl silicates, tetramethoxyorthosilicates, methyltrimethoxyorthosilicates, tetraalkoxyorthosilicates, trialkoxyorthosilicates, pressure sensitive silicone adhesives (such as BioPSA from Dow-Corning), and polyvinyl amines.

The gelling agent according to some embodiments of the present disclosure may include a polymer selected from any of synthetic or semi-synthetic polymeric materials, polyacrylate copolymers, cellulose derivatives and polymethyl vinyl ether/maleic anhydride copolymers. In some embodiments, the hydrophilic polymer comprises a polymer that is a high molecular weight (i.e., molar masses of more than about 5,000, and in some instances, more than about 10,000, or about 100,000, or about 1,000,000) and/or cross-linked polyacrylic acid polymer.

In some embodiments, the gelling agent comprises a carbomer. Carbomers are synthetic high molecular weight polymer of acrylic acid that are cross-linked with either allylsucrose or allylethers of pentaerythritol having a molecular weight of about $3 \times 10^6$. The gelation mechanism depends on neutralization of the carboxylic acid moiety to form a soluble salt. The polymer is hydrophilic and produces sparkling clear gels when neutralized. Carbomer gels possess good thermal stability in that gel viscosity and yield value are essentially unaffected by temperature. As a topical product, carbomer gels possess optimum rheological properties. The inherent pseudoplastic flow permits immediate recovery of viscosity when shear is terminated and the high yield value and quick break make it ideal for dispensing. Aqueous solution of Carbopol® is acidic in nature due to the presence of free carboxylic acid residues. Neutralization of this solution cross-links and gelatinizes the polymer to form a viscous integral structure of desired viscosity.

Carbomers are available as fine white powders which disperse in water to form acidic colloidal suspensions (a 1% dispersion has a pH of approximately 3) of low viscosity. Neutralization of these suspensions using a base, for example sodium, potassium or ammonium hydroxides, low molecular weight amines and alkanolamines, results in the formation of translucent gels. Nicotine salts such as nicotine chloride form stable water-soluble complexes with carbomers at about pH 3.5 and are stabilized at an optimal pH of about 5.6.

In some embodiments of the disclosure, the carbomer is Carbopol®. Such polymers are commercially available from B.F. Goodrich or Lubrizol under the designation Carbopol® 71G NF, 420, 430, 475, 488, 493, 910, 934, 934P, 940, 971PNF, 974P NF, 980 NF, 981 NF and the like. Carbopols are versatile controlled-release polymers, as described by Brock (Pharmacotherapy, 14:430-7 (1994), incorporated herein by reference) and Durrani (Pharmaceutical Res. (Supp.) 8:S-135 (1991), incorporated herein by reference), and belong to a family of carbomers which are synthetic, high molecular weight, non-linear polymers of acrylic acid, crosslinked with polyalkenyl polyether. In some embodiments, the carbomer is Carbopol® 974P NF, 980 NF, 5984 EP, ETD 2020NF, Ultrez 10 NF, 934 NF, 934P NF or 940 NF. In some embodiments, the carbomer is Carbopol® 980 NF, ETD 2020 NF, Ultrez 10 NF, Ultrez 21 or 1382 Polymer, 1342 NF, 940 NF. In some embodiments, about 0.05% to about 10%, about 0.5% to about 5%, or about 1% to about 3% by weight of the total composition of a high molecular weight carbopol can be present as the gelling agent. In some embodiments, the biophotonic composition of the disclosure comprises from about 0.05% to about 10%, from about 0.5% to about 5%, or from about 1% to about 3% by weight of the total composition of a high molecular weight carbopol.

In some embodiments, the gelling agent comprises a hygroscopic and/or a hydrophilic material useful for their water attracting properties. The hygroscopic or hydrophilic material may include, but is not limited to, glucosamine, glucosamine sulfate, polysaccharides, cellulose derivatives (hydroxypropyl methylcellulose, hydroxyethyl cellulose, hydroxypropyl cellulose, methylcellulose and the like), non-cellulose polysaccharides (galactomannans, guar gum, carob gum, gum arabic, sterculia gum, agar, alginates and the like), glycosaminoglycan, poly(vinyl alcohol), poly(2-hydroxyethylmethylacrylate), polyethylene oxide, collagen, chitosan, alginate, a poly(acrylonitrile)-based hydrogel, poly(ethylene glycol)/poly(acrylic acid) interpenetrating polymer network hydrogel, polyethylene oxide-polybutylene terephthalate, hyaluronic acid, high-molecular-weight polyacrylic acid, poly(hydroxy ethylmethacrylate), poly(ethylene glycol), tetraethylene glycol diacrylate, polyethylene glycol methacrylate, and poly(methyl acrylate-co-hydroxyethyl acrylate). In some embodiments, the hydrophilic gelling agent is selected from glucose, modified starch, methyl cellulose, carboxymethyl cellulose, propyl cellulose, hydroxypropyl cellulose, carbomers, alginic acid, sodium alginate, potassium alginate, ammonium alginate, calcium alginate, agar, carrageenan, locust bean gum, pectin, and gelatin.

The gelling agent may be protein-based/naturally derived material such as sodium hyaluronate, gelatin or collagen, lipids, or the like. The gelling agent may be a polysaccharide such as starch, chitosan, chitin, agarose, agar, locust bean gum, carrageenan, gellan gum, pectin, alginate, xanthan, guar gum, and the like.

In some embodiments, the composition can include up to about 2% by weight of the final composition of sodium hyaluronate as the single gelling agent. In some embodiments, the composition can include more than about 4% or more than about 5% by weight of the final composition of gelatin as the single gelling agent. In some embodiments, the composition can include up to about 10% or up to about 8% starch as the single gelling agent. In some embodiments, the composition can include more than about 5% or more than about 10% by weight of the total composition of collagen as the gelling agent. In some embodiments, about 0.1% to about 10% or about 0.5% to about 3% by weight of the total composition of chitin can be used as the gelling agent. In some embodiments, about 0.5% to about 5% by weight of the total composition of corn starch or about 5% to about 10% by weight of the total composition of corn starch can be used as the gelling agent. In some embodiments, more than about 2.5 wt % by weight of the total composition of alginate can be used in the composition as the gelling agent. In some embodiments, the percentages by weight percent of the total composition of the gelling agents can be as follows: cellulose gel (from about 0.3% to about 2.0%), konjac gum (from about 0.5% to about 0.7%), carrageenan gum (from about 0.02% to about 2.0%), xanthan gum (from about 0.01% to about 2.0%), acacia gum (from about 3% to about 30%), agar (from about 0.04% to about 1.2%), guar gum (from about 0.1% to about 1%), locust bean gum (from about 0.15% to about 0.75%), pectin (from about 0.1% to about 0.6%), tara gum (from about 0.1% to about 1.0%), polyvinylpyrrolidone (from about 1% to about 5%), sodium polyacrylate (from about 1% to about 10%). Other gelling agents can be used in amounts sufficient to gel the composition or to sufficiently thicken the composition. It will be appreciated that lower amounts of the above gelling agents may be used in the presence of another gelling agent or a thickener.

In some embodiments, the biophotonic composition of the present disclosure may be further encapsulated, e.g., in a membrane. Such a membrane may be transparent, and/or substantially, or fully impermeable. The membrane may be impermeable to liquid but permeable to gases such as air. In some embodiments, the composition may form a membrane that encapsulates the chromophore(s) of the biophotonic topical composition, where the membrane may be substantially impermeable to liquid and/or gas. The membrane may be formed of one or more lipidic agents, polymers, gelatin, cellulose or cyclodextrins, or the like. In some embodiments, the membrane is translucent or transparent to allow light to infiltrate to and from the chromophore(s). In some embodiments, the composition is a dendrimer with an outer membrane comprising poly(propylene amine). In some embodiments, the outer membrane comprises gelatin.

Polyols

According to some embodiments, the biophotonic compositions of the present disclosure may optionally further comprise one or more polyols. Suitable polyols that may be included in the composition include, but are not limited to a diol, a triol, a saccharide, glycerine, butane-1,2,3-triol, butane-1,2,4-triol, hexane-1,2,6-triol, propylene glycol, butanediol, butenediol, butynediol, pentanediol, hexanediol, octanediol, neopentyl glycol, 2-methyl-1,3-propanediol, diethylene glycol, triethylene glycol, tetraethylene glycol, dipropylene glycol and dibutylene glycol. In some embodiments when the biophotonic composition of the disclosure includes one or more polyols, the polyol is glycerine. In some embodiments when the biophotonic composition of the disclosure includes one or more polyols, the polyol is propylene glycol. In some embodiments when the biophotonic composition of the disclosure includes one or more polyols, the polyol is a combination of glycerine and propylene glycol.

In some embodiments, one or more polyols are present in an amount of about 5-75% by weight of the total composition, such as 5-75% by weight of the total composition. In some embodiments, one or more polyols are present in an amount of about 10-75% by weight of the total composition, such as 10-75% by weight of the total composition. In some embodiments, one or more polyols are present in an amount of about 15-75% by weight of the total composition, such as 15-75% by weight of the total composition. In some embodiments, one or more polyols are present in an amount of about 20-75% by weight of the total composition, such as 20-75% by weight of the total composition.

Antimicrobials

According to some embodiments, the biophotonic compositions of the present disclosure may optionally further comprise one or more antimicrobials. Antimicrobials kill microbes or inhibit their growth or accumulation. Exemplary antimicrobials (or antimicrobial agent) are recited in U.S. Patent Application Publication Nos. 20040009227 and 20110081530. Suitable antimicrobials for use in the methods of the present disclosure include, but not limited to, phenolic and chlorinated phenolic and chlorinated phenolic compounds, resorcinol and its derivatives, bisphenolic compounds, benzoic esters (parabens), halogenated carbonilides, polymeric antimicrobial agents, thazolines, trichloromethylthioimides, natural antimicrobial agents (also referred to as "natural essential oils"), metal salts, and broad-spectrum antibiotics.

Specific phenolic and chlorinated phenolic antimicrobial agents that can be used in the disclosure include, but are not limited to: phenol; 2-methyl phenol; 3-methyl phenol; 4-methyl phenol; 4-ethyl phenol; 2,4-dimethyl phenol; 2,5-dimethyl phenol; 3,4-dimethyl phenol; 2,6-dimethyl phenol; 4-n-propyl phenol; 4-n-butyl phenol; 4-n-amyl phenol; 4-tert-amyl phenol; 4-n-hexyl phenol; 4-n-heptyl phenol; mono- and poly-alkyl and aromatic halophenols; p-chlorophenyl; methyl p-chlorophenol; ethyl p-chlorophenol; n-propyl p-chlorophenol; n-butyl p-chlorophenol; n-amyl p-chlorophenol; sec-amyl p-chlorophenol; n-hexyl p-chlorophenol; cyclohexyl p-chlorophenol; n-heptyl p-chlorophenol; n-octyl; p-chlorophenol; o-chlorophenol; methyl o-chlorophenol; ethyl o-chlorophenol; n-propyl o-chlorophenol; n-butyl o-chlorophenol; n-amyl o-chlorophenol; tert-amyl o-chlorophenol; n-hexyl o-chlorophenol; n-heptyl o-chlorophenol; o-benzyl p-chlorophenol; o-benxyl-m-methyl p-chlorophenol; o-benzyl-m,m-dimethyl, p-chlorophenol; o-phenylethyl p-chlorophenol; o-phenylethyl-m-methyl p-chlorophenol; 3-methyl p-chlorophenol 3,5-dimethyl p-chlorophenol, 6-ethyl-3-methyl p-chlorophenol, 6-n-propyl-3-methyl p-chlorophenol; 6-iso-propyl-3-methyl p-chlorophenol; 2-ethyl-3,5-dimethyl p-chlorophenol; 6-sec-butyl-3-methyl p-chlorophenol; 2-iso-propyl-3,5-dimethyl p-chlorophenol; 6-diethylmethyl-3-methyl p-chlorophenol; 6-iso-propyl-2-ethyl-3-methyl p-chlorophenol; 2-sec-amyl-3,5-dimethyl p-chlorophenol; 2-diethylmethyl-3,5-dimethyl p-chlorophenol; 6-sec-octyl-3-methyl p-chlorophenol; p-chloro-m-cresol p-bromophenol; methyl p-bromophenol; ethyl p-bromophenol; n-propyl p-bromophenol; n-butyl p-bromophenol; n-amyl p-bromophenol; sec-amyl p-bromophenol; n-hexyl p-bromophenol; cyclohexyl p-bromophenol; o-bromophenol; tert-amyl o-bromophenol; n-hexyl o-bromophenol; n-propyl-m,m-dimethyl o-bromophenol; 2-phenyl phenol; 4-chloro-2-methyl phenol; 4-chloro-3-methyl phenol; 4-chloro-3,5-dimethyl phenol;

2,4-dichloro-3,5-dimethylphenol; 3,4,5,6-tetabromo-2-methylphenol; 5-methyl-2-pentylphenol; 4-isopropyl-3-methylphenol; para-chloro-metaxylenol (PCMX); chlorothymol; phenoxyethanol; phenoxyisopropanol; and 5-chloro-2-hydroxydiphenylmethane.

Resorcinol and its derivatives can also be used as antimicrobial agents. Specific resorcinol derivatives include, but are not limited to: methyl resorcinol; ethyl resorcinol; n-propyl resorcinol; n-butyl resorcinol; n-amyl resorcinol; n-hexyl resorcinol; n-heptyl resorcinol; n-octyl resorcinol; n-nonyl resorcinol; phenyl resorcinol; benzyl resorcinol; phenylethyl resorcinol; phenylpropyl resorcinol; p-chlorobenzyl resorcinol; 5-chloro-2,4-dihydroxydiphenyl methane; 4'-chloro-2,4-dihydroxydiphenyl methane; 5-bromo-2,4-dihydroxydiphenyl methane; and 4'-bromo-2,4-dihydroxydiphenyl methane.

Specific bisphenolic antimicrobial agents that can be used in the disclosure include, but are not limited to: 2,2'-methylene bis-(4-chlorophenol); 2,4,4'trichloro-2'-hydroxydiphenyl ether, which is sold by Ciba Geigy, Florham Park, N.J. under the trade name Triclosan®; 2,2'-methylene bis-(3,4,6-trichlorophenol); 2,2'-methylene bis-(4-chloro-6-bromophenol); bis-(2-hydroxy-3,5-dichlorophenyl)sulphide; and bis-(2-hydroxy-5-chlorobenzyl)sulphide.

Specific benzoic esters (parabens) that can be used in the disclosure include, but are not limited to: methylparaben; propylparaben; butylparaben; ethylparaben; isopropylparaben; isobutylparaben; benzylparaben; sodium methylparaben; and sodium propylparaben.

Specific halogenated carbanilides that can be used in the disclosure include, but are not limited to: 3,4,4'-trichlorocarbanilides, such as 3-(4-chlorophenyl)-1-(3,4-dichlorphenyl)urea sold under the tradename Triclocarban® by Ciba-Geigy, Florham Park, N.J.; 3-trifluoromethyl-4,4'-dichlorocarbanilide; and 3,3',4-trichlorocarbanilide.

Specific polymeric antimicrobial agents that can be used in the disclosure include, but are not limited to: polyhexamethylene biguanide hydrochloride; and poly(iminoimidocarbonyl iminoimidocarbonyl iminohexamethylene hydrochloride), which is sold under the tradename Vantocil® IB.

Specific thazolines that can be used in the disclosure include, but are not limited to that sold under the tradename Micro-Check®; and 2-n-octyl-4-isothiazolin-3-one, which is sold under the tradename Vinyzene® IT-3000 DIDP.

Specific trichloromethylthioimides that can be used in the disclosure include, but are not limited to: N-(trichloromethylthio)phthalimide, which is sold under the tradename Fungitrol®; and N-trichloromethylthio-4-cyclohexene-1,2-dicarboximide, which is sold under the tradename Vancide®.

Specific natural antimicrobial agents that can be used in the disclosure include, but are not limited to, oils of: anise, lemon, orange, rosemary, wintergreen, thyme, lavender, cloves, hops, tea tree, citronella, wheat, barley, lemongrass, cedar leaf, cedarwood, cinnamon, fleagrass, geranium, sandalwood, violet, cranberry, eucalyptus, vervain, peppermint, gum benzoin, basil, honey, fennel, fir, balsam, menthol, ocmea origanuin, hydastis, carradensis, Berberidaceac daceae, Ratanhiae longa, and Curcuma longa. Also included in this class of natural antimicrobial agents are the key chemical components of the plant oils which have been found to provide antimicrobial benefit. These chemicals include, but are not limited to: anethol, catechole, camphene, thymol, eugenol, eucalyptol, ferulic acid, farnesol, hinokitiol, tropolone, limonene, menthol, methyl salicylate, carvacol, terpineol, verbenone, berberine, ratanhiae extract, caryophellene oxide, citronellic acid, curcumin, nerolidol, and geraniol.

Specific metal salts that can be used in the disclosure include, but are not limited to, salts of metals in Groups 3a-5a, 3b-7b, and 8 of the periodic table. Specific examples of metal salts include, but are not limited to, salts of: aluminum, zirconium, zinc, silver, gold, copper, lanthanum, tin, mercury, bismuth, selenium, strontium, scandium, yttrium, cerium, praseodymiun, neodymium, promethum, samarium, europium, gadolinium, terbium, dysprosium, holmium, erbium, thalium, ytterbium, lutetium, and mixtures thereof. An example of the metal-ion based antimicrobial agent is sold under the tradename HealthShield®, and is manufactured by HealthShield Technology, Wakefield, Mass.

Specific broad-spectrum antimicrobial agents that can be used in the disclosure include, but are not limited to, those that are recited in other categories of antimicrobial agents herein.

Additional antimicrobial agents that can be used in the methods of the disclosure include, but are not limited to: pyrithiones, and in particular pyrithione-including zinc complexes such as these sold under the tradename Octopirox®; dimethyidimethylol hydantoin, which is sold under the tradename Glydant®; methylchloroisothiazolinone/methyl-isothiazolinone, which is sold under the tradename Kathon CG®; sodium sulfite; sodium bisulfite; imidazolidinyl urea, which is sold under the tradename Germall 115®; diazolidinyl urea, which is sold under the tradename Germall 11®; benzyl alcohol v2-bromo-2-nitropropane-1,3-diol, which is sold under the tradename Bronopol®; formalin or formaldehyde; iodopropenyl butylcarbamate, which is sold under the tradename Polyphase P100®; chloroacetamide; methanamine; methyldibromonitrile glutaronitrile (1,2-dibromo-2,4-dicyanobutane), which is sold under the tradename Tektamer®; glutaraldehyde; 5-bromo-5-nitro-1,3-dioxane, which is sold under the tradename Bronidox®; phenethyl alcohol; o-phenylphenol/sodium o-phenylphenol sodium hydroxymethylglycinate, which is sold under the tradename Suttocide A®; polymethoxy bicyclic oxazolidine; which is sold under the tradename Nuosept C®; dimethoxane; thimersal; dichlorobenzyl alcohol; captan; chlorphenenesin; dichlorophene; chlorbutanol; glyceryl laurate; halogenated diphenyl ethers; 2,4,4'-trichloro-2'-hydroxy-diphenyl ether, which is sold under the tradename Triclosan® and is available from Ciba-Geigy, Florham Park, N.J.; and 2,2'-dihydroxy-5,5'-dibromo-diphenyl ether.

Additional antimicrobial agents that can be used in the methods of the disclosure include those disclosed by U.S. Pat. Nos. 3,141,321; 4,402,959; 4,430,381; 4,533,435; 4,625,026; 4,736,467; 4,855,139; 5,069,907; 5,091,102; 5,639,464; 5,853,883; 5,854,147; 5,894,042; and 5,919,554, and U.S. Pat. Appl. Publ. Nos. 20040009227 and 20110081530, the contents of all of which are incorporated herein by reference.

Additional Components

The compositions, methods, and uses of the disclosure can also include other ingredients such as humectants (e.g., glycerine, ethylene glycol, and propylene glycol), preservatives such as parabens, and pH adjusters such as sodium hydroxide, sodium bicarbonate, and HCl.

In some embodiments, the pH of the composition is in or adjusted to the range of about 4 to about 10, such as from about 4 to about 9, from about 4 to about 8, from about 4 to about 7, from about 4 to 6.5, from about 4 to about 6, from about 4 to 5.5, from 4 to 5. In some embodiments, the pH of the composition is in or adjusted to the range of from about 4 to about 9. In some embodiments, the pH of the composition is in or adjusted to the range of from about 4 to about 8. In some embodiments, the pH of the composition is within the range of from about 4 to about 7. In some embodiments, the pH of the composition is within the range of about from 4 to about 6.5. In some embodiments, the pH of the composition is within the range of from about 4 to about 6. In some embodiments, the pH of the composition is within the range of from about 4 to about 5.5. In some embodiments, the pH of the composition is within the range of from about 4 to about 5. In some embodiments, the pH of the composition is within the range of about 5.0 to about 8.0, such as from about 6.0 to about 8.0, from about 6.5 to about 7.5, from about 5.5 to about 7.5. In some embodiments, the pH of the composition is within the range of from about 6.0 to about 8.0. In some embodiments, the pH of the composition is within the range of from about 6.5 to about 7.5. In some embodiments, the pH of the composition is within the range of from about 5.5 to about 7.5.

In some embodiments, the pH of the composition is in or adjusted to the range of from 4 to 10, such as from 4 to 9, from 4 to 8, from 4 to 7, from 4 to 6.5, from 4 to 6, from 4 to 5.5, from 4 to 5, from 5.0 to 8.0, from 6.0 to 8.0, from 6.5 to 7.5, from 5.5 to 7.5. In some embodiments, the pH of the composition is in or adjusted to the range of 4 to 9. In some embodiments, the pH of the composition is in or adjusted to the range of 4 to 8. In some embodiments, the pH of the composition is within the range of 4 to 7. In some embodiments, the pH of the composition is within the range of 4 to 6.5. In some embodiments, the pH of the composition is within the range of 4 to 6. In some embodiments, the pH of the composition is within the range of 4 to 5.5. In some embodiments, the pH of the composition is within the range of 4 to 5. In some embodiments, the pH of the composition is within the range of 5.0 to 8.0. In some embodiments, the pH of the composition is within the range of 6.0 to 8.0. In some embodiments, the pH of the composition is within the range of 6.5 to 7.5. In some embodiments, the pH of the composition is within the range of 5.5 to 7.5.

In some embodiments, the biophotonic compositions of the disclosure also include an aqueous substance (such as water) or an alcohol. Alcohols include, but are not limited to, ethanol, propanol, isopropanol, butanol, iso-butanol, t-butanol or pentanol. In some embodiments, the chromophore or combination of chromophores is in solution in a medium of the biophotonic composition. In some embodiments, the chromophore or combination of chromophores is in solution in a medium of the biophotonic composition, wherein the medium is an aqueous substance.

Methods of use and Treatment
Photoactivation

The biophotonic compositions suitable for use in the methods of the present disclosure may be selected from any of the embodiments of the biophotonic compositions described above. For instance, the biophotonic compositions useful in the method of the present disclosure may comprise a chromophore, such as a chromophore that undergoes at least partial photobleaching upon application of light. The chromophore may absorb at a wavelength of from about 200 nm to about 800 nm, such as, from about 200 nm to about 700 nm, from about 200 nm to about 600 nm or from about 200 nm to about 500 nm. In some embodiments, the chromophore absorbs at a wavelength of from about 200 nm to about 600 nm. In some embodiments, the chromophore absorbs light at a wavelength of from about 200 nm to about 300 nm, from about 250 nm to about 350 nm, from about 300 nm to about 400 nm, from about 350 nm to about 450 nm, from about 400 nm to about 500 nm, from about 450 nm to about 650 nm, from about 600 nm to about 700 nm, from about 650 nm to about 750 nm or from about 700 nm to about 800 nm. In some embodiments, suitable biophotonic compositions for the methods of the present disclosure may further comprise at least one additional chromophore (e.g., a second chromophore). The absorption spectrum of the second chromophore overlaps at least about 80%, about 70%, about 60%, about 50%, about 40%, about 30%, or about 20% with the emission spectrum of the first chromophore. In some embodiments, the first chromophore has an emission spectrum that overlaps at least about 1-10%, about 5-15%, about 10-20%, about 15-25%, about 20-30%, about 25-35%, about 30-40%, about 35-45%, about 50-60%, about 55-65% or about 60-70% with an absorption spectrum of the second chromophore.

Illumination of the biophotonic composition with light may cause a transfer of energy from the first chromophore to the second chromophore. Subsequently, the second chromophore may emit energy as fluorescence and/or generate reactive oxygen species. In some embodiments of the methods the present disclosure, energy transfer caused by the application of light is not accompanied by concomitant generation of heat, or does not result in tissue damage.

In the methods of the present disclosure, any source of actinic light can be used to illuminate the biophotonic compositions. Any type of halogen, LED or plasma arc lamp or laser may be suitable. The primary characteristic of suitable sources of actinic light will be that they emit light in a wavelength (or wavelengths) appropriate for activating the one or more photoactivators present in the composition. In some embodiments, an argon laser is used. In some embodiments, a potassium-titanyl phosphate (KTP) laser (e.g., a GreenLight™ laser) is used. In another embodiment, sunlight may be used. In some embodiments, a LED photocuring device is the source of the actinic light. In some embodiments, the source of the actinic light is a source of light having a wavelength from about 200 nm to about 800 nm. In some embodiments, the source of the actinic light is a source of visible light having a wavelength between about 400 nm and about 700 nm. In some embodiments, the source of the actinic light is a source of visible light having a wavelength between about 400 nm and about 600 nm. In some embodiments, the source of the actinic light is a source of visible light having a wavelength between about 400 nm and about 550 nm. In some embodiments, the source of the actinic light is a source of visible light having a wavelength between about 380 nm and about 700 nm. In some embodiments, the source of the actinic light is a source of visible light having a wavelength between about 380 nm and about 600 nm. In some embodiments, the source of the actinic light is a source of visible light having a wavelength between about 380 nm and about 550 nm. In some embodiments, the source of the actinic light is a source of light having a wavelength between 200 nm to 800 nm. In some embodiments, the source of the actinic light is a source of visible light having a wavelength between 400 nm and 700 nm. In some embodiments, the source of the actinic light is a source of visible light having a wavelength between 400 nm and 600 nm. In some embodiments, the source of the actinic light is a source of visible light having a wavelength between 400 nm and 550 nm. In some embodiments, the source of the actinic light is a source of visible light having a wavelength between 380 nm and 700 nm. In some embodiments, the source of the actinic light is a source of visible light having a wavelength between 380 nm and 600 nm. In some embodiments, the source of the actinic light is a source of visible light having a wavelength between 380 nm and 550 nm. In some embodiments, the biophotonic composition of the disclosure is illuminated with violet and/or blue light. Furthermore, the source of actinic light should have a suitable power density. Suitable power density for non-collimated light sources (LED, halogen or plasma lamps) are in the range from about 1 mW/cm$^2$ to about 1200 mW/cm$^2$, such as from about 50 mW/cm$^2$ to about 1000 mW/cm$^{2'}$ from 100 mW/cm$^2$ to about 900 mW/cm$^2$, from 200 mW/cm$^2$ to about 800 mW/cm$^2$, or from about 1 mW/cm$^2$ to about 200 mW/cm$^2$. In some embodiments, suitable power density for non-collimated light sources (LED, halogen or plasma lamps) are in the range from about 1 mW/cm$^2$ to about 200 mW/cm$^2$. In some embodiments, suitable power density for laser light sources is in the range from about 0.5 mW/cm$^2$ to about 0.8 mW/cm$^2$.

In some embodiments of the methods of the present disclosure, the light has an energy at the patient's skin of from about 1 mW/cm$^2$ to about 500 mW/cm$^2$, or about 1-300 mW/cm$^2$, or about 1-200 mW/cm$^2$, wherein the energy applied depends at least on the condition being treated, the wavelength of the light, the distance of the patient's skin from the light source, and the thickness of the biophotonic composition. In some embodiments, the light at the patient's skin is from about 1 to about 40 mW/cm$^2$, or about 20-60 mW/cm$^2$, or about 40-80 mW/cm$^2$, or about 60-100 mW/cm$^2$, or about 80-120 mW/cm$^2$, or about 100-140 mW/cm$^2$, or about 120-160 mW/cm$^2$, or about 140-180 mW/cm$^2$, or about 160-200 mW/cm$^2$, or about 110-240 mW/cm$^2$, or about 110-150 mW/cm$^2$, or about 190-240 mW/cm$^2$.

In some embodiments, a mobile device can be used to activate embodiments of the biophotonic composition of the present disclosure, wherein the mobile device can emit light having an emission spectrum which overlaps an absorption spectrum of the chromophore in the biophotonic composition. The mobile device can have a display screen through which the light is emitted and/or the mobile device can emit light from a flashlight which photoactivates the biophotonic composition.

In some embodiments, a display screen on a television or a computer monitor can be used to activate the biophotonic composition, wherein the display screen can emit light having an emission spectrum which overlaps an absorption spectrum of a photoactive agent in the photoactivatable composition.

In some embodiments, the chromophore or combination of chromophores can be photoactivated by ambient light which may originate from the sun or other light sources. Ambient light can be considered to be a general illumination that comes from all directions in a room that has no visible source. In some embodiments, the chromophore or combination of chromophores can be photoactivated by light in the visible range of the electromagnetic spectrum. Exposure times to ambient light may be longer than that to direct light.

In some embodiments, different sources of light can be used to activate the biophotonic compositions, such as a combination of ambient light and direct LED light.

The duration of the exposure to actinic light required will be dependent on the surface of the treated area, the severity of the condition that is being treated, the power density, wavelength and bandwidth of the light source, the thickness of the biophotonic composition, and the treatment distance from the light source. The illumination of the treated area by fluorescence may take place within seconds or even fragment of seconds, but a prolonged exposure period is beneficial to exploit the synergistic effects of the absorbed, reflected and reemitted light on the composition of the present disclosure and its interaction with the tissue being treated. In some embodiments, the time of exposure to actinic light of the tissue or skin or wound on which the biophotonic composition has been applied is a period from about 1 second to about 60 minutes. In some embodiments, the time of exposure to actinic light of the tissue or skin or wound on which the biophotonic composition has been applied is a period from about 1 minute to about 60 minutes. In some embodiments, the time of exposure to actinic light of the tissue, skin or wound on which the biophotonic composition has been applied is a period from about 1 minute to about 5 minutes. In some embodiments, the time of exposure to actinic light of the tissue, skin or wound on which the biophotonic composition has been applied is a period from about 1 minute and 5 minutes. In another embodiment, the time of exposure is from about 1 second to about 5 minutes or from about 60 seconds to about 5 minutes. In another embodiment, the time of exposure to actinic light of the tissue on which the biophotonic composition has been applied is a period of less than about 5 minutes. In another embodiment, the time of exposure is from about 1 second to about 5 minutes, or from about 60 seconds and about 5 minutes per cm$^2$ of the area to be treated, so that the total time of exposure of a 10 cm$^2$ area would be from 10 minutes and 50 minutes.

In some embodiments, the biophotonic composition is illuminated for a period from about 1 minute to about 3 minutes. In some embodiments, light is applied for a period from about 1 to about 30 seconds, from about 1 to about 60 seconds, from about 15 seconds to about 45 seconds, from about 30 seconds to about 60 seconds, from about 0.75 minute to about 1.5 minutes, from about 1 minute to about 2 minutes, from about 1.5 minute to about 2.5 minutes, from about 2 minutes to about 3 minutes, from about 2.5 minutes to about 3.5 minutes, from about 3 minutes to about 4 minutes, from about 3.5 minutes to about 4.5 minutes, from about 4 minutes to about 5 minutes, from about 5 minutes to about 10 minutes, from about 10 minutes to about 15 minutes, from about 15 minutes to about 20 minutes, from about 20 minutes to about 25 minutes, or from about 20 minutes to about 30 minutes. In some embodiments, light is applied for a period of about 1 second. In some embodiments, light is applied for a period of about 5 seconds. In some embodiments, light is applied for a period of about 10 seconds. In some embodiments, light is applied for a period of about 20 seconds. In some embodiments, light is applied for a period of about 30 seconds. In some embodiments, the biophotonic composition is illuminated for a period less than about 60 minutes. In some embodiments, the biophotonic composition is illuminated for a period less than about 30 minutes. In some embodiments, the biophotonic composition is illuminated for a period less than about 20 minutes. In some embodiments, the biophotonic composition is illuminated for a period less than about 15 minutes. In some embodiments, the biophotonic composition is illuminated for a period less than about 10 minutes. In some embodiments, the biophotonic composition is illuminated for a period less than about 5 minutes. In some embodiments, the biophotonic composition is illuminated for a period less than about 1 minute. In some embodiments, the biophotonic composition is illuminated for a period less than about 30 seconds. In some embodiments, the biophotonic composition is illuminated for a period less than about 20 seconds. In some embodiments, the biophotonic composition is illuminated for a period less than about 10 seconds. In some embodiments, the biophotonic composition is illuminated for a period less than about 5 seconds. In some embodiments, the biophotonic composition is illuminated for a period less than about 1 second. In some embodiments, the source of actinic light is in continuous motion over the treated area for the appropriate time of exposure. In some embodiments, multiple applications of the biophotonic composition and actinic light are performed. In some embodiments, the tissue, skin or wound is exposed to actinic light at least two, three, four, five or six times. In some embodiments, the tissue, skin or wound is exposed to actinic light at least two, three, four, five or six times with a resting period in between each exposure. In certain such embodiments, the resting period is less than about 1 minute, less than about 5 minutes, less than about 10 minutes, less than about 20 minutes, less about 40 minutes, less than about 60 minutes, less than about 2 hours, less than about 4 hours, less than about 6 hours, or less than 12 hours. In some embodiments, the entire treatment may be repeated in its entirety as may be required by the patient. In some embodiments, a fresh application of the biophotonic composition is applied before another exposure to actinic light.

In the methods of the present disclosure, the biophotonic composition may be optionally removed from the site of treatment following application of light. In some embodiments, the biophotonic composition is left on the treatment site for more than about 30 minutes, more than one hour, more than about 2 hours, more than about 3 hours. It can be illuminated with ambient light. To prevent drying, the composition can be covered with a transparent or translucent cover such as a polymer film, or an opaque cover which can be removed before illumination.

For any of the methods described herein, the embodiments of this disclosure contemplate the use of any of the compositions, or mixtures of them, described throughout the application. In addition, in various embodiments of any of the methods described herein, combinations of any step or steps of one method with any step or steps from another method may be employed.

Otitis Externa

The biophotonic compositions and methods of the present disclosure are useful to treat otitis externa. Therefore, it is an objective of the present disclosure to provide a method of providing biophotonic therapy to a target site, wherein the method is for the treatment of otitis externa. In certain embodiments, the otitis externa is chronic or relapsing otitis externa.

Otitis externa is an inflammation or infection of the external auditory canal, the auricle (pinna), or both. Causes of otitis externa in mammals include, but are not limited to, allergies, such as atopy or food allergies; parasites, such as ear mites; microorganisms, such as bacteria and yeast or other fungi; foreign bodies; trauma; the ear environment, e.g., excess moisture and ear anatomy; hereditary or immune conditions; and tumors. The condition is often chronic and one of the main aspects involved in the chronicity of the disease is the presence of infections caused by bacteria resistant to different antibiotics (e.g., *Pseudomonas aeruginosa*).

Otitis externa is one of the most common conditions seen in cats and dogs. Symptoms of otitis externa in cats and dogs include odor, scratching or rubbing of ears and head, discharge in the ears, redness or swelling of the ear canal, shaking of the head or tilting it to one side, pain around the ears, and changes in behavior such as depression or irritability.

Otitis externa is also a common condition in humans. Symptoms of otitis externa in humans include otalgia, hearing loss, ear pressure, narrowing of the ear canal, tinnitus, fever, itching, pain, and discharge.

In some aspects, the disclosure provides a method of treating otitis externa comprising: applying a biophotonic composition to a patient in need thereof, wherein the biophotonic composition comprises at least one oxidant and at least one chromophore capable of activating the oxidant; and exposing said biophotonic composition to actinic light for a time sufficient for said chromophore to cause activation of said oxidant. In certain such aspects, the patient is a mammal, such as a human, a feline or a canine. In certain such aspects, the otitis externa is chronic otitis externa. In certain such aspects, the method is performed once per week for one or more weeks, such as once per week for one week, two weeks, three weeks, four weeks, five weeks, or six weeks, or up to what is deemed appropriate by the physician or veterinarian. In certain such aspects, the method is performed twice per week for one or more weeks, such as twice per week for one week, two weeks, three weeks, four weeks, five weeks, or six weeks, or up to what is deemed appropriate by the physician or veterinarian.

In other aspects, the disclosure provides for the use of a biophotonic composition for the manufacture of a medicament for treating a patient afflicted with otitis externa, wherein said composition comprises: at least one oxidant, and at least one chromophore capable of activating the oxidant; in association with a pharmacologically acceptable carrier. In certain such aspects, the patient is a mammal, such as a human, a feline or a canine. In certain such aspects, the otitis externa is chronic otitis externa.

In some aspects, the disclosure provides for use of a biophotonic composition for the treatment of a patient afflicted with otitis externa, wherein said composition comprises: at least one oxidant; and at least one chromophore capable of activating the oxidant; in association with a pharmacologically acceptable carrier. In certain such aspects, the patient is a mammal, such as a human, a feline or a canine. In certain such aspects, the otitis externa is chronic otitis externa.

In some embodiments, the biophotonic compositions of the disclosure may be applied at regular intervals such as one or more times per week, and/or at an interval deemed appropriate by the physician or veterinarian. In some embodiments, the biophotonic compositions of the disclosure are applied once per week for one or more weeks, such as once per week for one week. In some embodiments, the biophotonic compositions of the disclosure are applied once per week for two weeks. In some embodiments, the biophotonic compositions of the disclosure are applied once per week for three weeks. In some embodiments, the biophotonic compositions of the disclosure are applied once per week for four weeks. In some embodiments, the biophotonic compositions of the disclosure are applied once per week for five weeks. In some embodiments, the biophotonic compositions of the disclosure are applied once per week for six weeks. In some embodiments, the biophotonic compositions of the disclosure are applied once per week for seven weeks. In some embodiments, the biophotonic compositions of the disclosure are applied once per week for eight or more weeks.

In some embodiments, the biophotonic compositions of the disclosure are applied twice per week for one or more weeks, such as twice per week for one week. In some embodiments, the biophotonic compositions of the disclosure are applied twice per week for two weeks. In some embodiments, the biophotonic compositions of the disclosure are applied twice per week for three weeks. In some embodiments, the biophotonic compositions of the disclosure are applied twice per week for four weeks. In some embodiments, the biophotonic compositions of the disclosure are applied twice per week for five weeks. In some embodiments, the biophotonic compositions of the disclosure are applied twice per week for six weeks. In some embodiments, the biophotonic compositions of the disclosure are applied twice per week for seven weeks. In some embodiments, the biophotonic compositions of the disclosure are applied twice per week for eight or more weeks.

In some embodiments, the biophotonic compositions of the disclosure are applied three times or more per week for one or more weeks, such as three times or more per week for one week, three times or more per week for two weeks. In some embodiments, the biophotonic compositions of the disclosure are applied three times or more per week for three weeks. In some embodiments, the biophotonic compositions of the disclosure are applied three times or more per week for four weeks. In some embodiments, the biophotonic compositions of the disclosure are applied three times or more per week for five weeks. In some embodiments, the biophotonic compositions of the disclosure are applied three times or more per week for six weeks. In some embodiments, the biophotonic compositions of the disclosure are applied three times or more per week for seven weeks. In some embodiments, the biophotonic compositions of the disclosure are applied three times or more per week for eight or more weeks.

In some embodiments, the biophotonic compositions and methods of the present disclosure are useful in treating otitis externa, for example, by ameliorating any symptom caused by a microorganism or inhibiting it from spreading. In some embodiments, the biophotonic compositions and methods of the present disclosure are useful in treating otitis externa, for example, by treating or preventing redness and swelling. In some embodiments, the biophotonic compositions and methods of the present disclosure are useful in treating otitis externa, for example, by treating or preventing discharge from the ear. In some embodiments, the biophotonic compositions and methods of the present disclosure are useful in treating otitis externa without the use of antibiotics.

Combination Therapies

Any of the biophotonic compositions, methods, or uses of this disclosure may be useful in combination with other therapeutics.

In some embodiments, the phrase "combination therapy" embraces the administration of any of the compositions described herein, and an additional therapeutic agent, or mixtures of them, as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. The therapeutic agents can be administered by the same route or by different routes. For example, a first therapeutic agent of the combination selected may be administered by intravenous injection or orally while the biophotonic composition of the disclosure is administered topically. Alternatively, for example, all therapeutic agents may be administered topically. The sequence in which the therapeutic agents are administered is not narrowly critical. "Combination therapy" also embraces the administration of the compositions as described herein in further combination with other biologically active ingredients (such as, but not limited to, a second and different therapeutic agent) and/or non-drug therapies (such as, but not limited to, surgery or radiation).

In some embodiments, the therapeutic agents administered in combination therapy simultaneously, separately, or sequentially with any of the compounds and compositions of this disclosure, or mixtures thereof, can comprise, but are not limited to: a non-steroidal anti-inflammatory drug (NSAID), an anti-inflammatory agent, a corticosteroid, an anti-allergic agent, a steroid drug, one or more of the antimicrobial agents described above, or mixtures thereof.

In some embodiments, any of the compositions described herein can allow the combination therapeutic agents and/or compositions described herein or mixtures thereof to be administered at a low dose, that is, at a dose lower than has been conventionally used in clinical situations.

Alternatively, the methods and combinations of this disclosure maximize the therapeutic effect at higher doses.

In some embodiments, when administered as a combination, the therapeutic agents can be formulated as separate compositions which are given at the same time or different times, or the therapeutic agents can be given as a single composition.

Kits

The present disclosure also provides kits for preparing and/or applying any of the compositions of the present disclosure for the treatment of otitis externa. The kit may include a biophotonic topical composition as described herein, a device for applying or removing the composition, instructions of use for the composition, and/or a light source. In some embodiments, the biophotonic composition comprises at least one oxidant and at least one chromophore capable of activating the oxidant.

In some embodiments, the kit includes more than one composition, for example, a first and a second composition. The first composition may include at least one chromophore capable of activating the oxidant and the second composition may include at least one oxidant. In certain such embodiments, the oxidant is chosen from hydrogen peroxide, carbamide peroxide and benzoyl peroxide. In certain such embodiments, the first and/or second composition further comprises one or more gelling agents.

In some embodiments, the first composition may comprise at least one chromophore capable of activating the oxidant in a liquid or as a powder, and the second composition may comprise at least one oxidant. In certain such embodiments, the oxidant is chosen from hydrogen peroxide, carbamide peroxide and benzoyl peroxide. In certain such embodiments, the first and/or second composition further comprises one or more gelling agents.

In some embodiments, the kit includes containers comprising the compositions of the present disclosure. In some embodiments, the kit includes a first container comprising the at least one chromophore capable of activating the oxidant, and a second container comprising at least one oxidant. In certain such embodiments, the oxidant is chosen from hydrogen peroxide, carbamide peroxide and benzoyl peroxide. In certain such embodiments, the first and/or second composition further comprises one or more gelling agents.

The containers may be light impermeable, air-tight, and/or leak resistant. Exemplary containers include, but are not limited to, syringes, vials, or pouches. The first and second compositions may be included within the same container but separated from one another until a user mixes the compositions. For example, in certain such embodiments, the container may be a dual-chamber syringe where the contents of the chambers mix on expulsion of the compositions from the chambers. In some embodiments, the pouch may include two chambers separated by a frangible membrane. In some embodiments, one component may be contained in a syringe and injectable into a container comprising the second component.

The biophotonic composition may also be provided in a container comprising one or more chambers for holding one or more components of the biophotonic composition, and an outlet in communication with the one or more chambers for discharging the biophotonic composition from the container.

In some embodiments, the kit comprises a systemic or topical drug for augmenting the treatment of the composition. In certain such embodiments, the kit may include a systemic or topical antibiotic or hormone treatment for otitis externa.

Written instructions on how to use the biophotonic composition in accordance with the present disclosure may be included in the kit, or may be included on or associated with the containers comprising the compositions of the present disclosure.

In some embodiments, the kit may comprise a further component which is a dressing. The dressing may be a porous or semi-porous structure for receiving the biophotonic composition. The dressing may comprise woven or non-woven fibrous materials.

In some embodiments of the kit, the kit may further comprise a light source such as a portable light with a wavelength appropriate to activate the chromophore in the biophotonic composition. The portable light may be battery operated or re-chargeable.

In some embodiments, the kit may further comprise one or more waveguides.

Identification of equivalent compositions, methods and kits are well within the skill of the ordinary practitioner and would require no more than routine experimentation, in light of the teachings of the present disclosure. Practice of the disclosure will be still more fully understood from the following examples, which are presented herein for illustration only and should not be construed as limiting the disclosure in any way.

EXAMPLES

The examples below are given so as to illustrate the practice of various embodiments of the present disclosure. They are not intended to limit or define the entire scope of this disclosure.

It should be appreciated that the disclosure is not limited to the particular embodiments described and illustrated herein but includes all modifications and variations falling within the scope of the disclosure as defined in the appended embodiments.

Evaluation of Treatment with Biophotonic Therapy in Canines and Felines

Studies were carried out to evaluate the efficacy and effectiveness of the biophotonic compositions of the present description in treatment of canine and feline chronic otitis externa in comparison to conventional therapy. These studies provided information regarding resistant bacterial complications in chronic or relapsing otitis externa, which is one of the most important causes of chronicity of the disease. In these studies, factors that contribute to the development of the biophotonic therapy in otitis externa were assessed. These factors included but were not limited to: viscosity, concentration, method of light-delivery, duration of radiation, and frequency of treatment. Results of treatment in these studies offered resolution of chronic or relapsing otitis externa bacterial complications.

Study Design

A randomized controlled clinical trial was conducted in dogs with clinically apparent, spontaneous, chronic and/or relapsed otitis externa with or without bacterial complications. After the integrity of the tympanic membrane was evaluated, dogs were divided into three groups: Group I (or Group QW)—treatment with biophotonic therapy once a week for six times (T0 to T5) and evaluated after each treatment; Group II (or Group BW)—treatment with biophotonic therapy twice a week for six times (T0-T5) and evaluated after each treatment; and Group III (or Group C)—treatment with a conventional therapy twice-a-day for two weeks and twice-a-week evaluation (T0 to T5). The biophotonic therapy was carried out with no concomitant antibiotic and anti-inflammatory therapy. The conventional therapy was a topical therapy with Baytril Otic® (emulsion containing enrofloxacin (5 mg/mL) and silver sulfadiazine (10 mg/mL) with benzyl alcohol (20 mg/mL), cetylstearyl alcohol in a neutral oil and purified water emulsion). In all three groups, before the first treatment, the external auditory channel was adequately cleaned. Ear swabs for bacterial culture and cytology were sampled prior to the treatment and once a week during the full length of the treatment.

Assessed Parameters and Tests

Clinical assessment included: (1) otitis index scoring system (OTIS-3) based on erythema, oedema/swelling, erosion/ulceratin, and exudate. The total score was between 0-12 (Nattal & Benisgnor, 2014); (2) Pruritus severity scale (VAS 0-10) (Hill et al., 2007, Rybnicek, et al., 2008; Hill et al., 2009); (3) Pain severity score (VAS 0-10) (Buback et al., 1996; Wolfe et al., 2006; Nutal & Bensignor, 2014); and (4) Actual temperatures (° C.) taken before and/or after treatment in exposed and contralateral ear canal (Grono, 1970; Cole, 2009; Mittal 2014). Preferably, temperatures may be taken before each application of the treatment with liquids (e.g., saline) or the biophotonic composition.

Cytological assessment included: (1) visual description of the cytological findings; and (2) otitis cytological scoring system (0-3) for presence of cells, earwax/cerumen, neutrophils, bacteria (e.g., rod shaped bacteria, coccoid bacteria), fungi, or yeast, etc.

Bacteriologic assessment included: (1) bacterial culture; (2) quantitative bacteriological assessment (measured by colony forming unit, CFU) for total bacterial counts and bacterial counts for each species in case of multiple isolations; and (3) antibiotic susceptibility testing.

Figure 4:
FIG. 4 is a photograph showing an ear swab taken in a canine patient for bacteriology assessment before treatment.

General Protocols for Each Treatment Session (1) Before treatment, perform ear swab for bacteriology assessment (FIG. 4)

Figure 5:
FIG. 5 is a photograph showing an ear swab taken in a canine patient for cytological assessment.

(2) Perform Ear swab for cytological assessment (FIG. 5)

Figure 6:
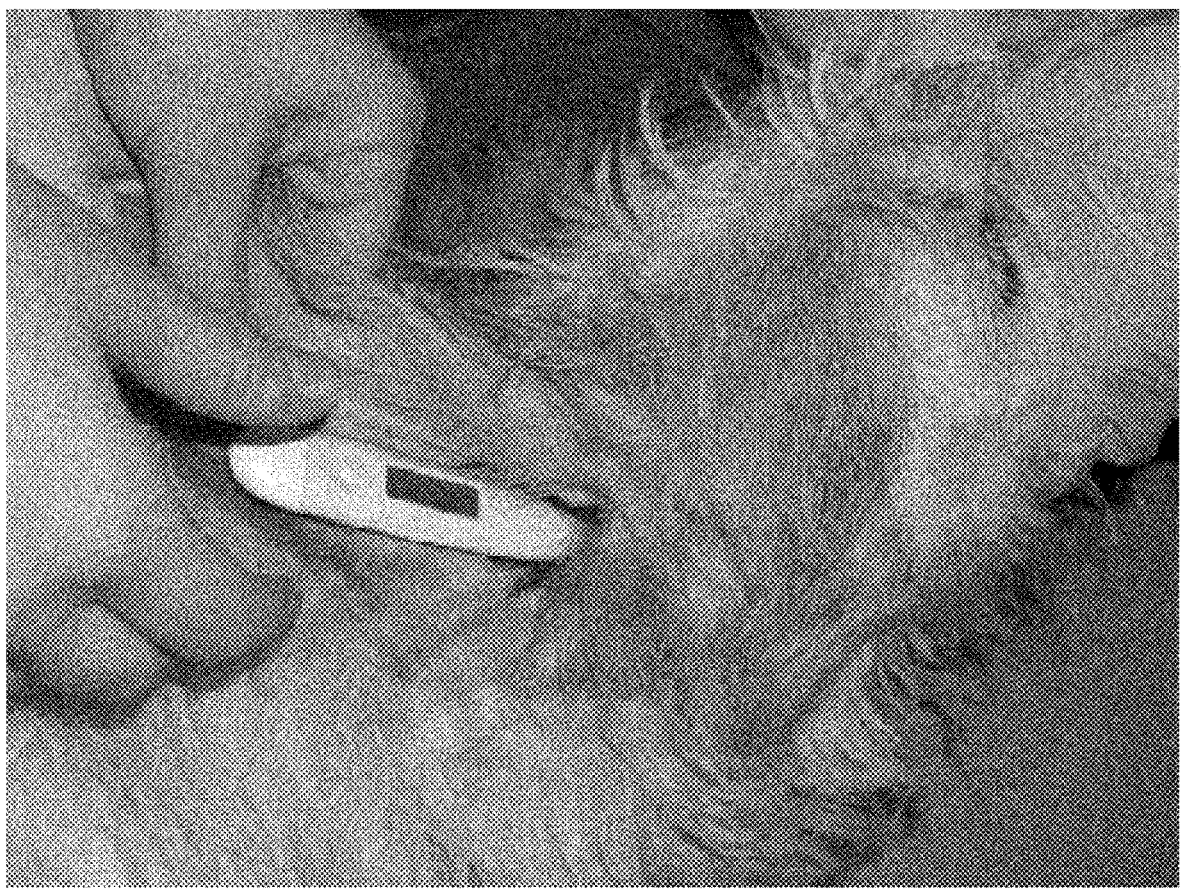
FIG. 6 is a photograph showing measuring aural temperature bilaterally in a canine patient before treatment.

(3) Before treatment, measure aural temperature bilaterally (FIG. 6)

Figure 7:
FIG. 7 is a photograph of the external meatus in a canine patient before treatment.

(4) Before treatment, take photographs of the external meatus (FIG. 7)

Figure 8A:
FIGS. 8A-8B is a photograph showing preparation and application of the therapeutic composition.
Figure 8B:
Figure 9:
FIG. 9 is a photograph showing irradiation of the treatment area of a canine patient with a Bluephase® lamp, a source of actinic light.

(5) Record otoscopy and attribution clinical score (6) Prepare therapeutic composition by mixing chromophore and urea peroxide (UP) (FIG. 8A); apply the therapeutic composition locally (FIG. 8B); illuminate the treated area with a Bluephase® lamp (Ivoclar Vivadent AG, FL-9494 Schaan, Liechtenstein), a source of actinic light (FIG. 9)

Figure 10:
FIG. 10 is a photograph showing an ear swab taken in a canine patient for bacteriologic assessment after treatment.

(7) Take an ear swab for bacteriologic assessment after treatment (FIG. 10)

Figure 11:
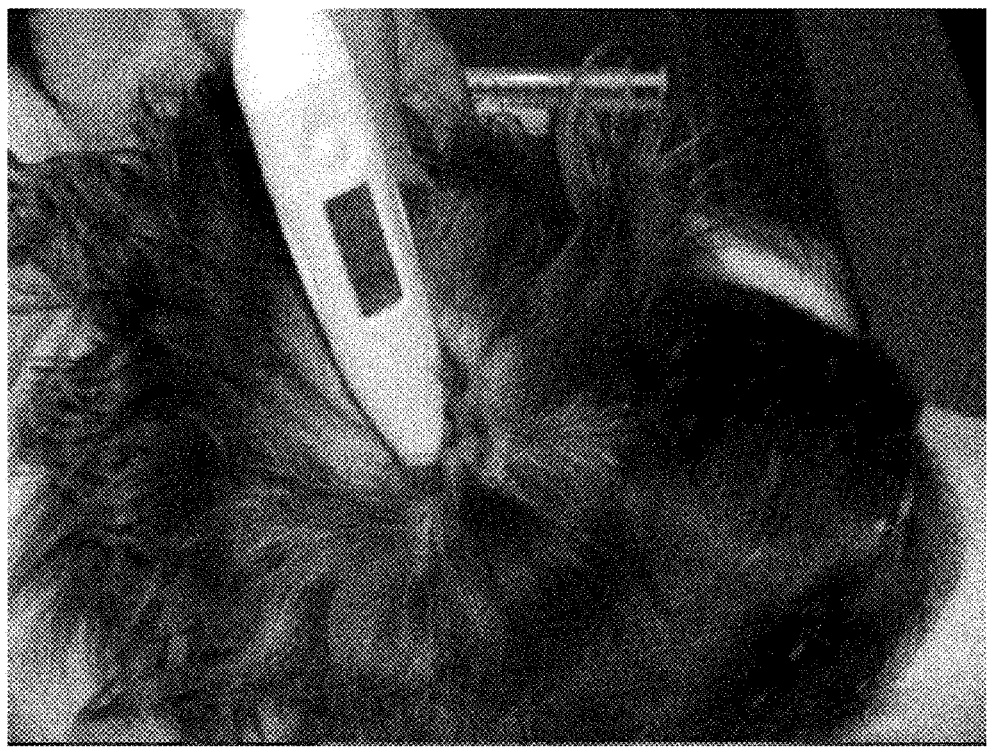
FIG. 11 is a photograph showing measuring aural temperature bilaterally in a canine patient after treatment.

(8) Measure aural temperature bilaterally after treatment (FIG. 11)

Figure 12:
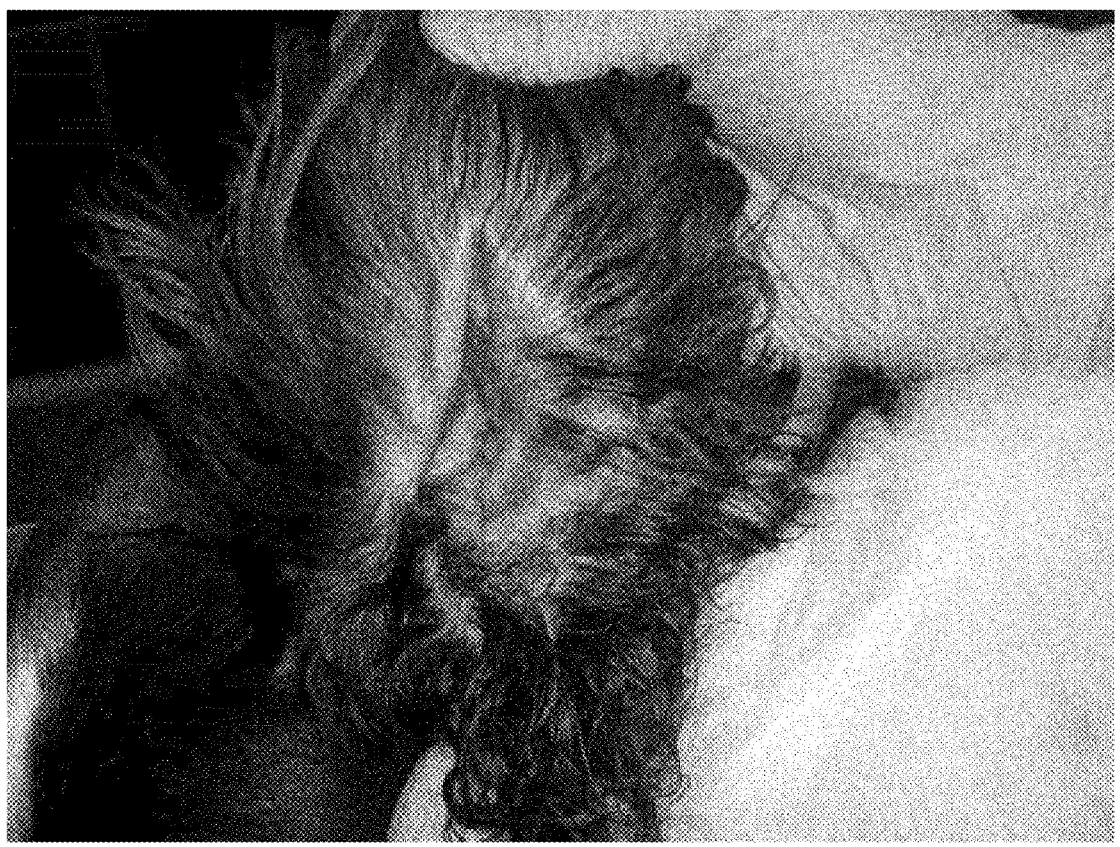
FIG. 12 is a photograph of the external meatus in a canine patient after treatment.

(9) Take a photograph of the external meatus after treatment (FIG. 12)

Results

Forty three (43) patients with otitis were recruited and divided into three groups: fifteen (15) cases in Group I (Group QW) and fourteen (14) cases in Group II (Group BW), and fourteen cases in Group III (Group C). The numbers of tests performed during the treatment totaled: 258 clinical assessments, 492 aural temperature assessments, 258 non-sterile ear swabs, 258 cytological assessments, 432 sterile ear swabs, 432 bacteriologic assessments (including cultures, identification, bacterial counts, and antibiotic susceptibility tests).

Treatments were provided with specifications according to the Table 1 below in order to establish a therapeutic protocol with respect to the viscosity of composition to be applied into the ear canal of the animal to be treated and to establish a suitable regimen with respect to an illumination of the applied composition once present in the ear canal to be treated.

TABLE 1

Test protocols for composition application for a treatment of canine otitis externa

| Formulation and Chromophore | % UP[a] | Light Source[b] | Illumination Time | Bluephase lamp light emission program[c] |
|---|---|---|---|---|
| Liquid, Eosin Y | 3 | Blue phase lamp | 10 sec | Soft Start |
| Liquid, Eosin Y | 6 | Blue phase lamp | 30 sec | Soft Start |
| Semi-liquid, Eosin Y | 6 | Blue phase lamp with multi-fiber | 4 min | High |
| Semi-liquid, Eosin Y | 6 | Blue phase lamp without multi-fiber | 2-3 min (in some instances, 1.5 min or 30 sec) | Soft Start + High[d] |

With reference to Table 1 above, the symbol "(a)" stands for urea peroxide (UP, carbamide peroxide) and % UP is the percent of UP by weight of the total composition. Symbol "(b)" denotes the use of photonic conductor, single-fiber or multi-fiber, to allow for a better distribution of light in the ear. It was found that it was not necessary to use a single-fiber or a coated multi-fiber photonic conductor for the biophotonic therapy. Symbol "(c)" indicates that multiple cycles were performed to achieve total illumination from 2 to 4 minutes as the maximum duration of emission of the light source was 30 seconds. Symbol "(d)" indicates the Bluephase® lamp illumination program that was utilized: Soft Start program in the first cycle, then High program in subsequent cycles. The Soft Start and High programs for the Bluephase® lamp are pre-set illumination programs that are programmed into the lamp by the manufacture and can be selected for use by following the manufacturer's instructions for use. For the Soft Start program, the lamp will proceed to increase the intensity of light in a step-by-step fashion, e.g., from about 650 mW/cm$^2$ to about 1200 mW/cm$^2$, whereas with the High program, the lamp will emit light at a consistently high level (e.g., approximately 1200 mW/cm$^2$) upon initiation of the illumination cycle.

Statistical analysis of data were carried our using Mann-Whitney rank sum test and Wilcoxon rank sum test for ordinal variables; Student t-test for cardinal variables. A difference with a p-value $<=0.05$ will be considered statistically significant.

An application of a composition of the present description in liquid form comprised a chromophore gel comprising a chromophore, a gelling agent (e.g., carbopol), and water; and a carrier gel comprising UP and water.

The semi-liquid form of the composition comprised a carrier gel and a chromophore gel. The carrier gel comprised UP, carbopol, and water and the chromophore gel comprised a chromophore, a gelling agent and water. Carbopol was present in an amount of 0.6% (on a % w/w basis of the total composition). The carrier gel and chromophore gel components of the composition had respective pH values of 5.24 and 5.09. The resulting biophotonic compositions for application to the patient's ear canal had a semi-liquid consistency due to the low carbopol concentration and low pH, thus, allowing for the composition to flow into the ear canal.

With respect to selecting a suitable protocol from those described in Table 1, the semi-liquid form of the composition was selected (see rows 4 and 5, Table 1) with a total illumination time of 2 to 4 minutes. The illumination program was:

1) A first 30 second illumination cycle using the Soft Start program, and

2) All subsequent illumination cycles using the High program.

For most treatment cases, a photonic conductor (light conducting) tip was attached to the illumination end of the lamp to achieve a greater depth of illumination within the ear canal and, thus, the applied composition.

(1) Results According to Clinical Score

Figure 13A:
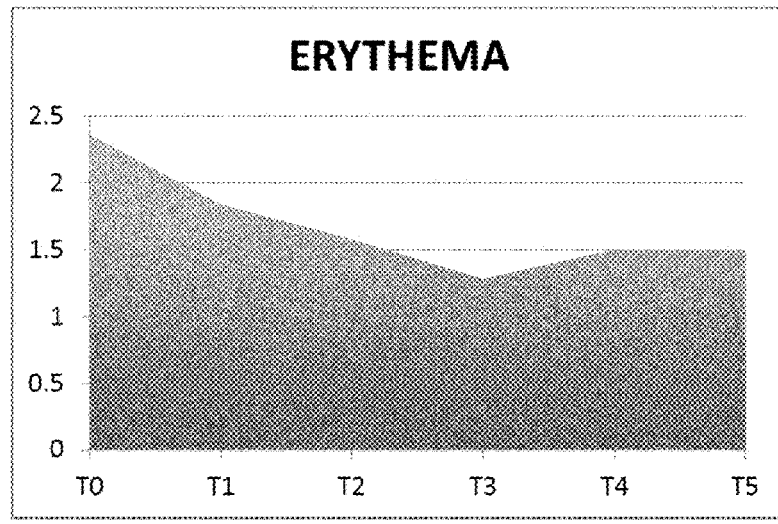
FIGS. 13A-13D present graphs of various clinical score assessment results in the canine patients following biophotonic treatment, with FIG. 13A showing erythema results, FIG. 13B showing oedema/swelling results, FIG. 13C showing erosion/ulceration results, and FIG. 13D showing exudate results.
Figure 13B:
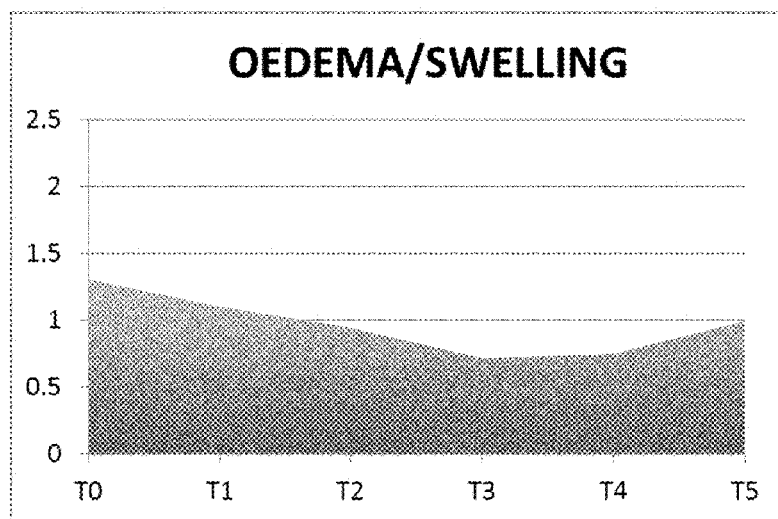
Figure 13C:
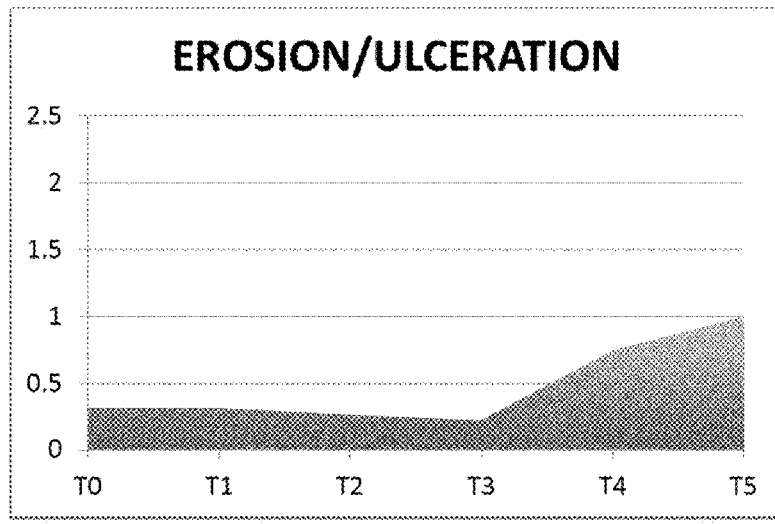
Figure 13D:
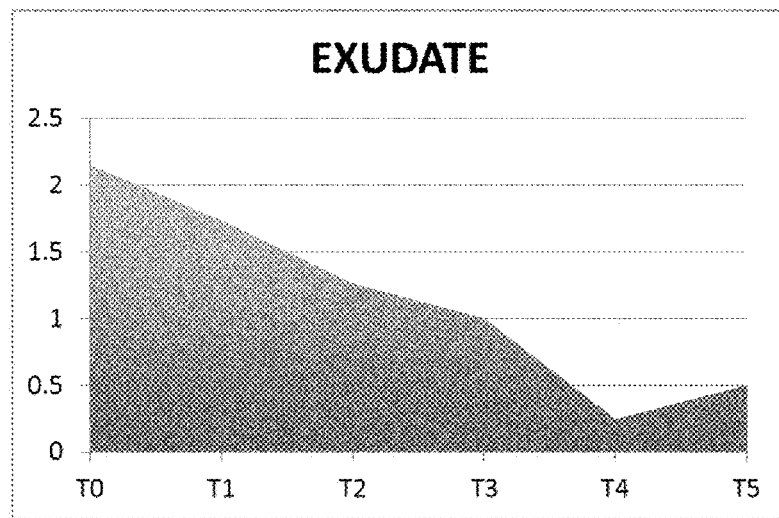

Results relating to a clinical score with respect to the canine patients treated with the biophotonic compositions of the present disclosure indicated that the treatment yielded positive improvement in the otitis condition of the patients treated with the biophotonic compositions of the present disclosure. As can be seen from FIG. 13A, the overall erythema (redness of the skin in the ear canal) score decreased in the treated animals, with a steep decline in the degree of redness occurring after the initial treatment. Regarding oedema/swelling and exudate (from the ear canal), both of these factors also decreased (see FIGS. 13B and 13D).

Figure 20A:
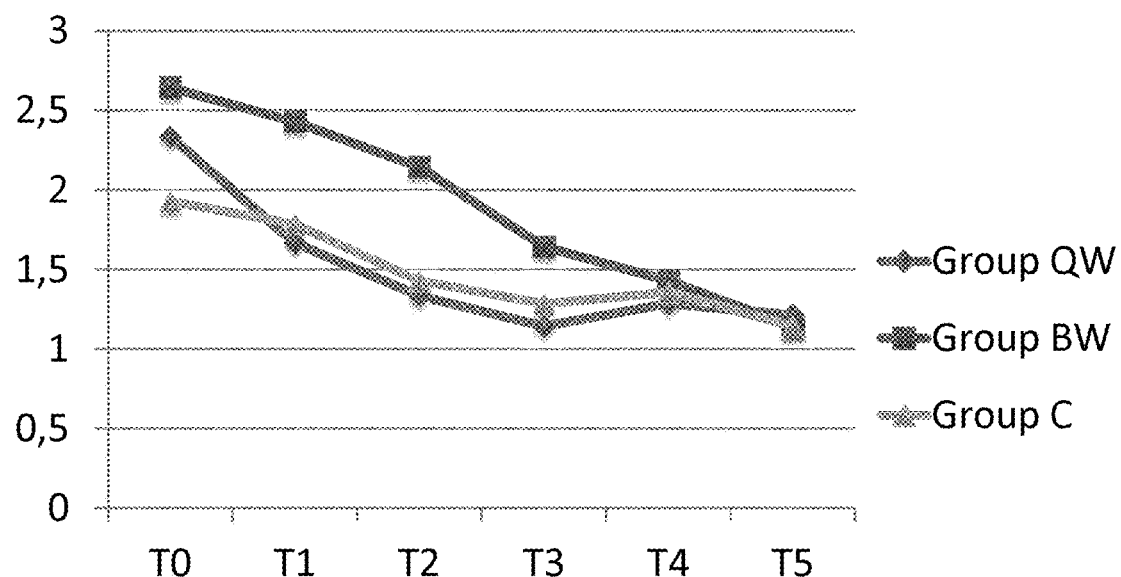
FIGS. 20A-20D present various clinical score assessment results of the canine patients in the randomized controlled clinical trial described in the Examples section of this disclosure.
Figure 20B:
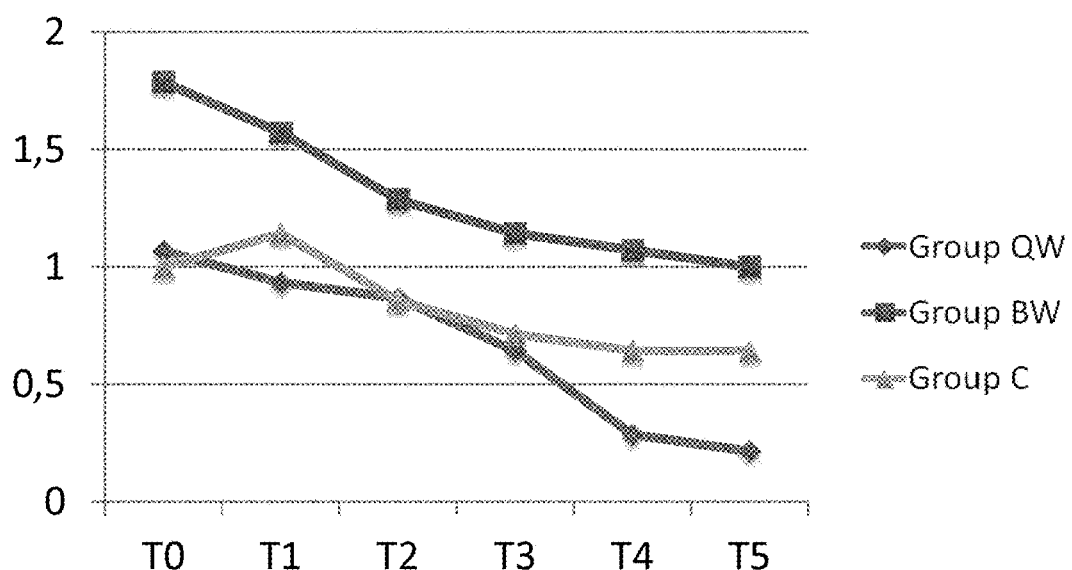
Figure 20C:
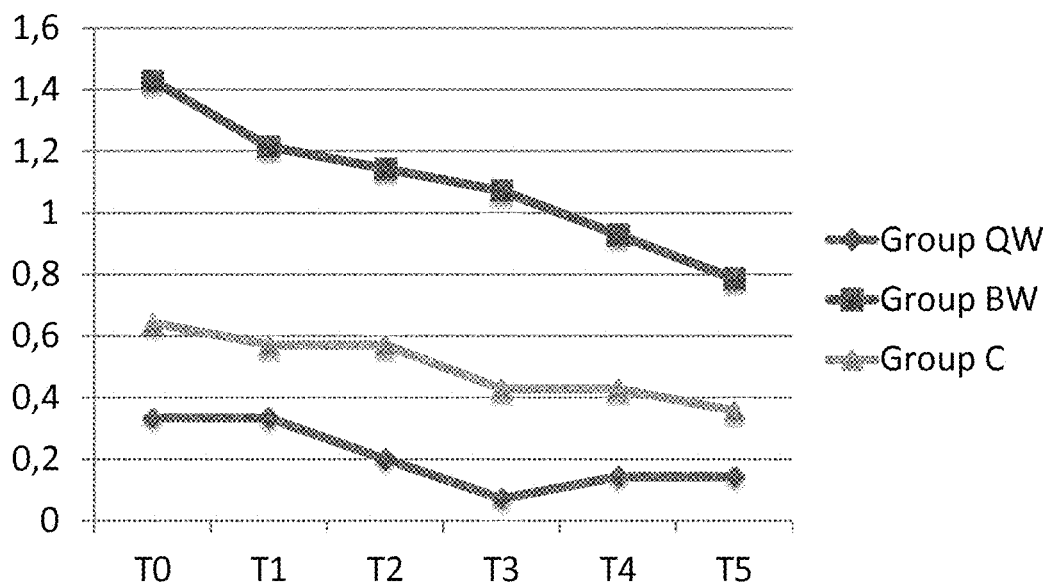
Figure 20D:
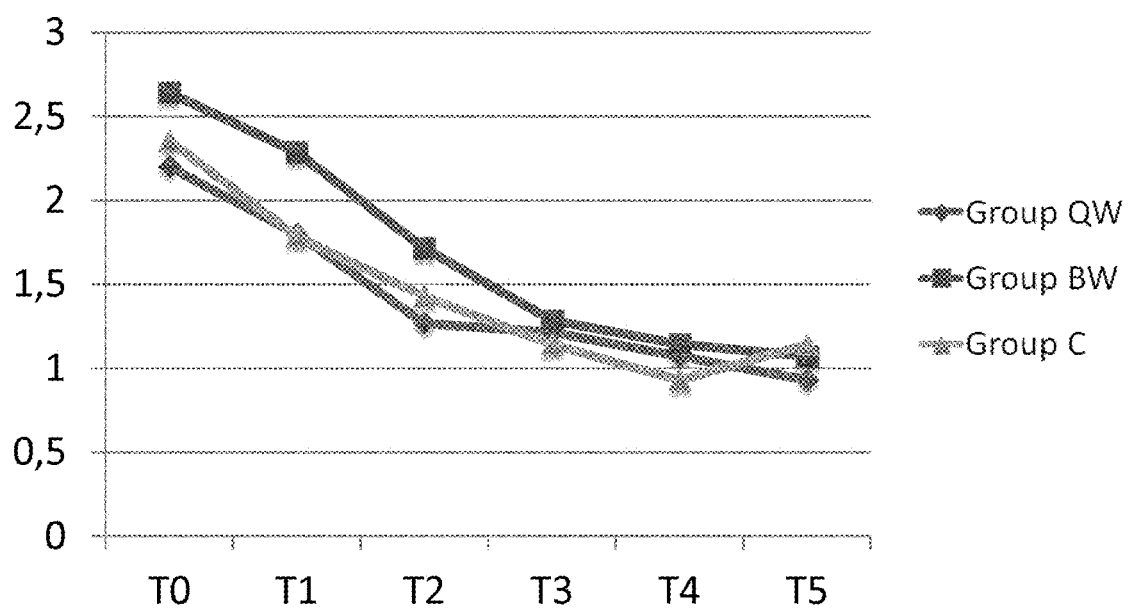

FIGS. 20A-20C present the data for all three Groups. In FIG. 20A, the overall erythema (redness of the skin in the ear canal) score decreased in patients of both Groups I (QW) and II (BW). For patients in Group I (QW), there was a steep decline in the degree of redness occurring after the initial treatment. Regarding the criteria of oedema/swelling, erosion/ulceration, and exudate (from the ear canal), all of these factors also showed a decrease in patients of both Group I (QW) and II (BW) (see FIGS. 20B, 20C, and 20D).

Figure 14:
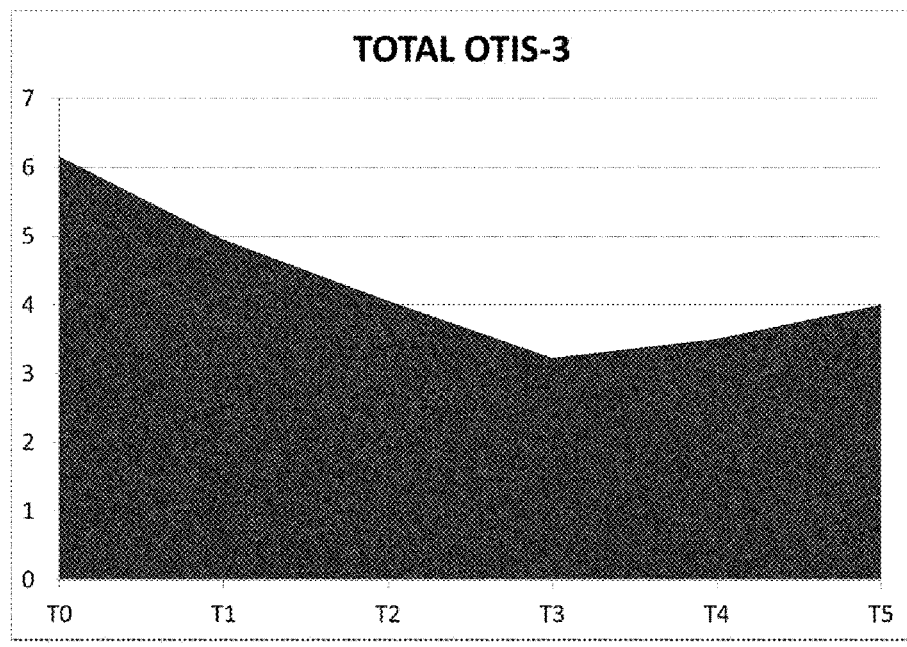
FIG. 14 presents a graph of the total OTIS-3 score in canine patients that had received biophotonic treatment.
Figure 21:
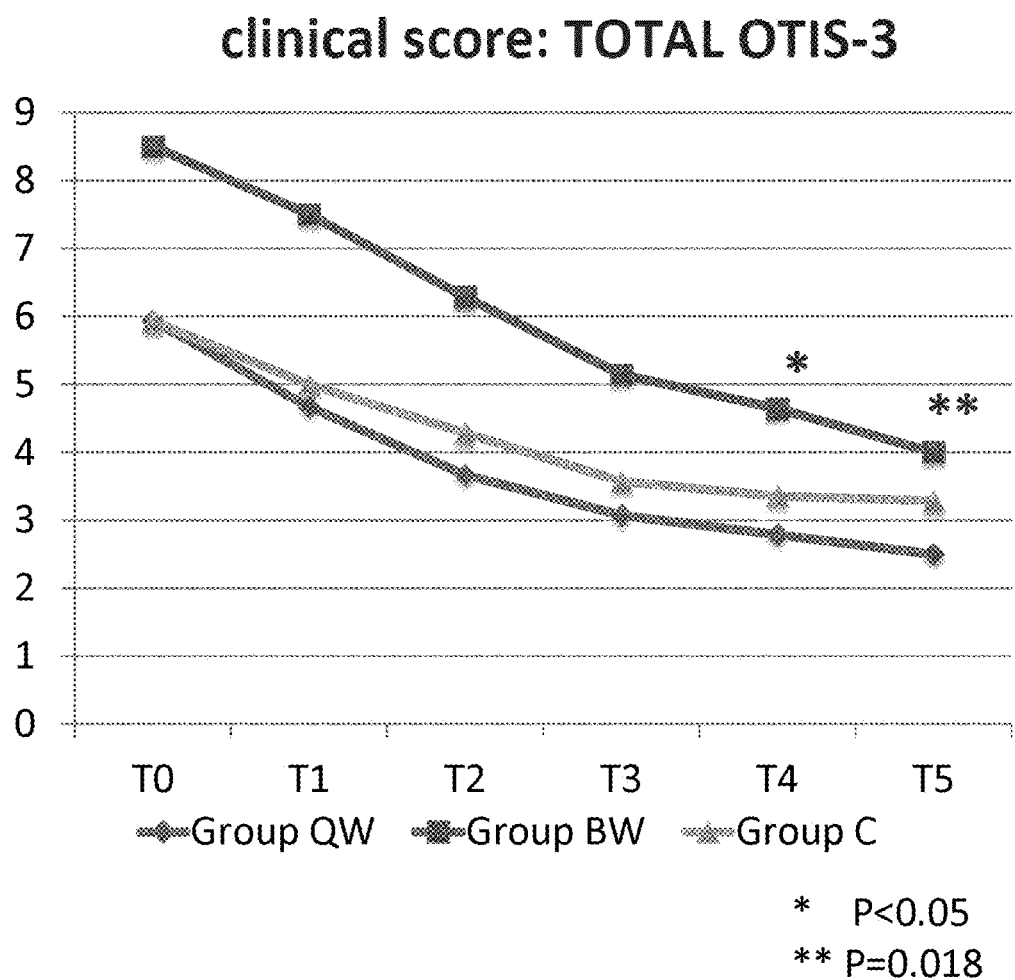
FIG. 21 presents the total OTIS-3 (otitis index scoring system) score in canine patients in Group I (Group QW), II (Group BW), and III (Group C) of the randomized controlled clinical trial described in the Examples section of this disclosure, respectively.

Combining the aforementioned four criteria to derive a total Otitis Index Score (OTIS-3) (See, Nuttall, T. and Bensignor E. "A pilot study to develop an objective clinical score for canine otitis externa," *Veterinary Dermatology*, 2014, volume 25(6), pages 530-e92, incorporated herein by reference), as can be seen in FIG. 14, indicates there was a steep decline in the score index up to the completion of the third treatment, with the decrease maintained after completion of the fifth treatment. The OTIS-3 score observed at the commencement of the treatment, these data indicate a marked improvement in the treated patients' otitis condition from a clinical criteria perspective. FIG. 21 indicates OTIS-3 scores for the three Groups. As one can see, a steep decline was observed in the score index in both Group I (QW) and Group II (BW). These data indicate a marked improvement in the treated patients' otitis condition from a clinical criteria perspective.

Figure 15A:
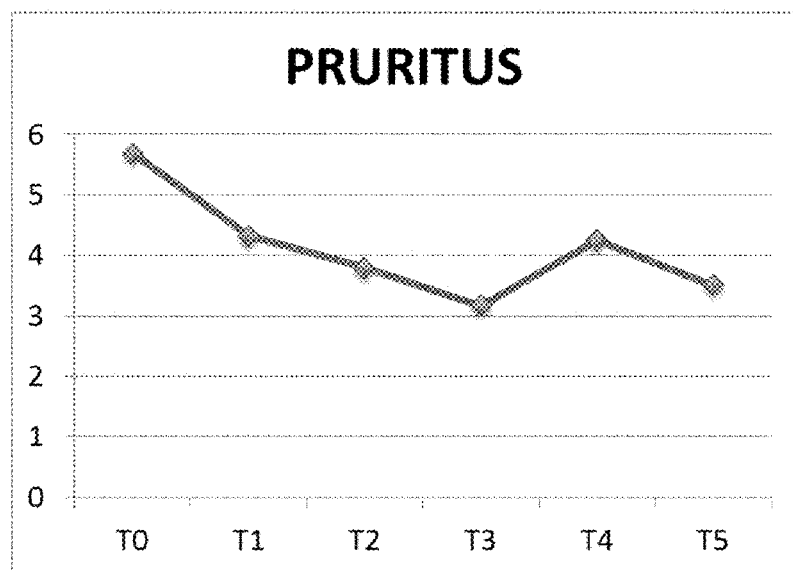
FIGS. 15A-15B present graphs of further clinical assessment criteria, with FIG. 15A showing pruritus results for canine patients, and FIG. 15B showing pain results for canine patients.
Figure 15B:
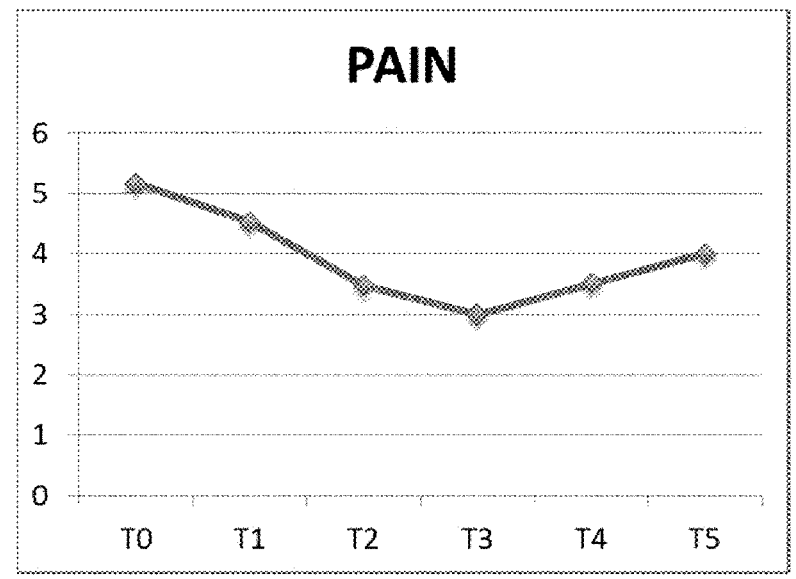
Figure 22A:
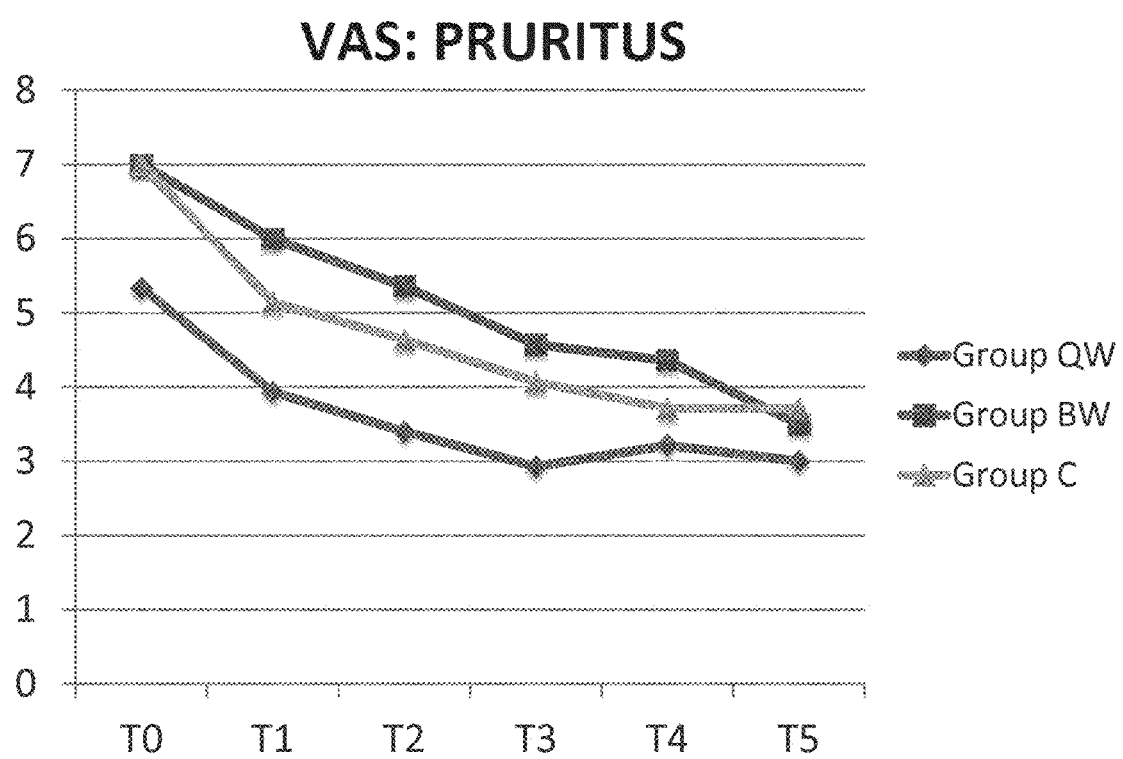
FIGS. 22A-22B present graphs of clinical assessment criteria, with FIG. 22A showing pruritus results for canine patients, and FIG. 22B showing pain results for canine patients.
Figure 22B:
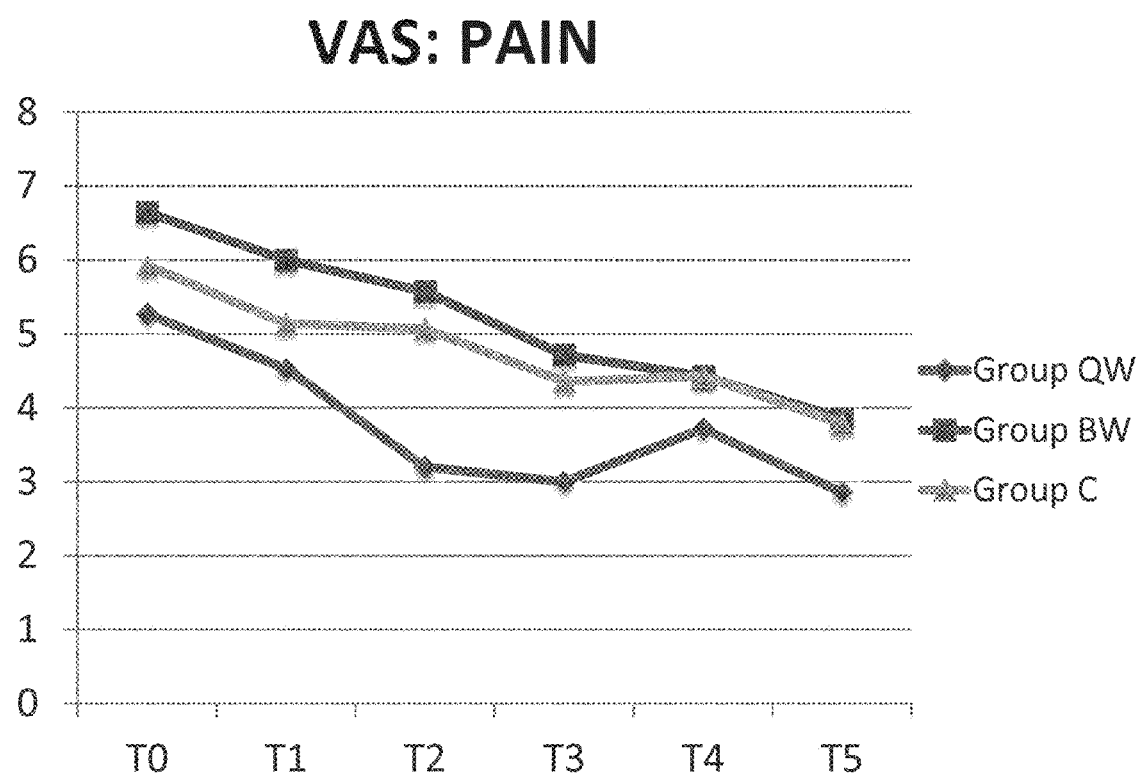

Data from other clinical criteria, such as an evaluation of pruritus (itchiness) using a pruritus severity scale (VAS 0-10) (see Hill P. B. et al. "Development of an owner-assessed scale to measure the severity of pruritus in dogs," *Veterinary Dermatology*, 2007, volume 18(5), pages 301-308; Rybníček, J. et al. "Further validation of a pruritus severity scale for use in dogs," *Veterinary Dermatology*, 2008, volume 20, pages 115-122, each reference incorporated herein by reference) and a pain severity score (VAS 0-10) (see Nuttall, T. and Bensignor E. 104, referenced above), were also evaluated, see FIG. 15A and FIG. 15B, respectively, and these criteria also showed an improvement over the course of the otitis treatment via a biophotonic therapy using the biophotonic compositions of the present description. In FIGS. 22 A and 22B, pruritus and pain data are presented for all three Group I (QW), Group II (BW), and Group III (C).

Figure 16A:
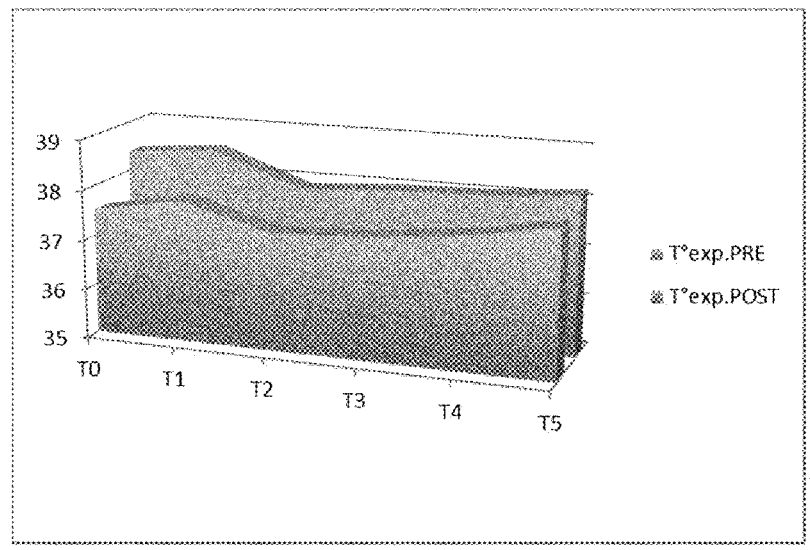
FIGS. 16A-16C present graphs of further clinical assessment criteria, with FIG. 16A showing aural temperature results in the canine patient population receiving the biophotonic composition treatment, FIG. 16B showing the aural temperature results in the control canine patient population, and FIG. 16C showing the treatment and control populations' aural temperature results in combination.
Figure 16B:
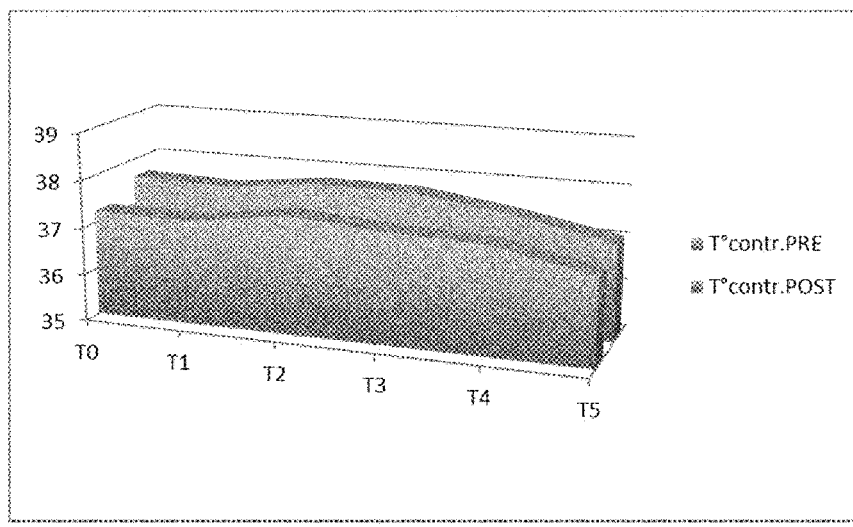
Figure 16C:
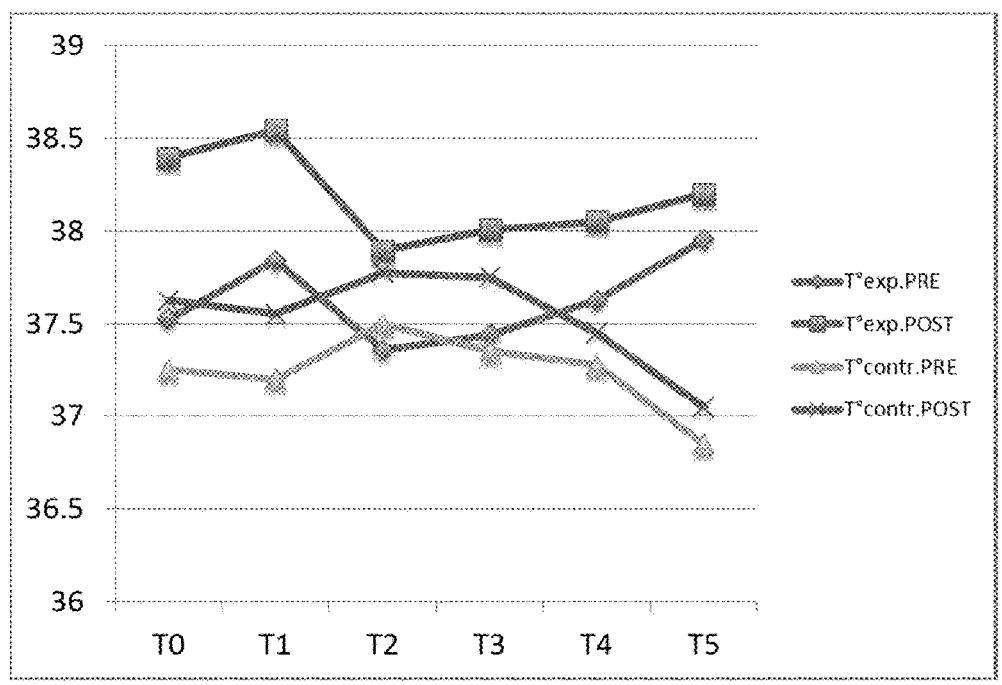

A further clinical evaluation was also measured, aural temperatures in the exposed and contralateral ear canals of patients both before and after treatment with the biophotonic compositions of the disclosure or treatment with a conventional therapy (see Grono L. R. "Studies of the microclimate of the external auditory canal in the dog. I. Aural Temperature," *Research in Veterinary Sciences*, 1970, volume 11(4), pages 307-311, incorporated herein by reference). The results from the dogs treated with the biophotonic compositions of the present disclosure are shown in FIG. 16A. The results from dogs treated with conventional therapy are shown in FIG. 16B. The post-treatment temperature for dogs receiving the biophotonic composition treatment showed a greater differential increase to the pre-treatment temperature versus the conventional therapy treated group, as illustrated in FIG. 16C.

(2) Results According to Cytological Scoring System

Results with respect to cytological scoring indicia, which included a neutrophil count score and an earwax/cerumen measurement score, along with a relative score measurement of rod shaped bacteria, coccoid bacteria and malassezia (to measure the presence of yeast in the ear canal), indicated that animals afflicted with otitis externa and treated with the biophotonic compositions of the present description showed an improvement in these indicia.

Figure 17A:
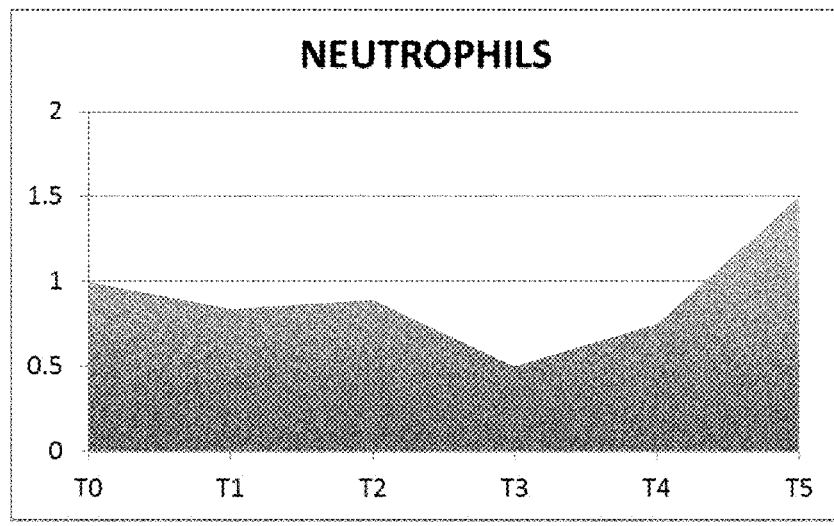
FIGS. 17A-17B present graphs of cytological assessment criteria, with FIG. 17A showing neutrophil results for canine patients, and FIG. 17B showing earwax/cerumen results for canine patients.
Figure 23A:
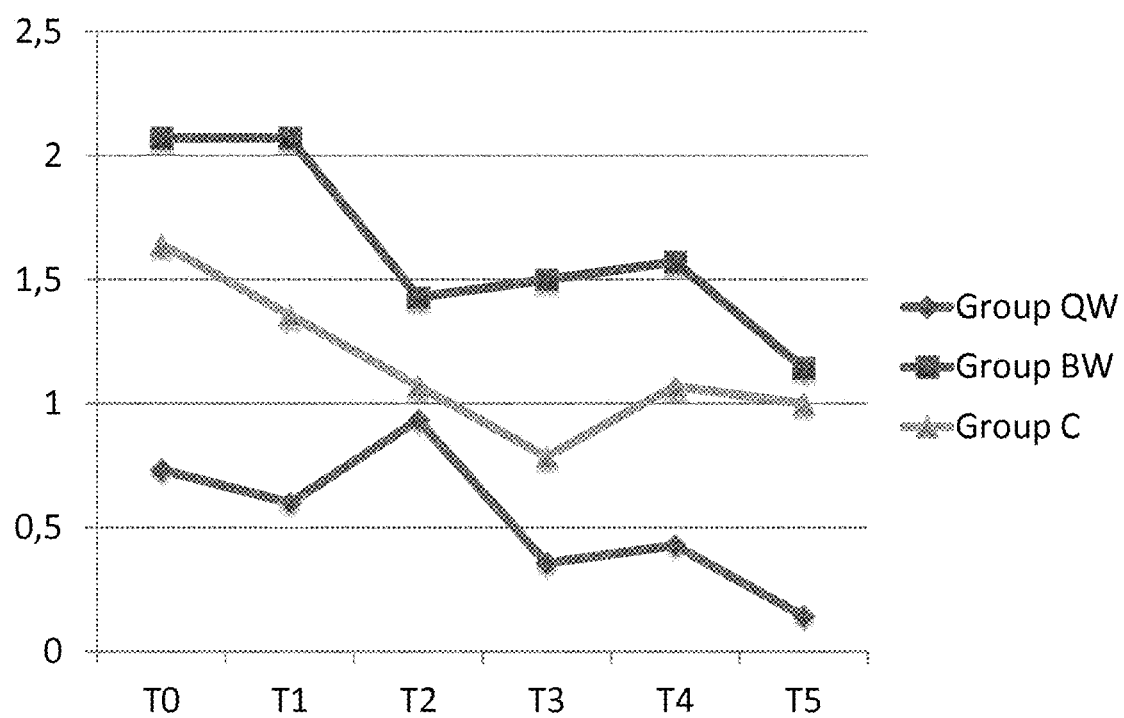
FIGS. 23A-23B present graphs of cytological assessment criteria, with FIG. 23A showing neutrophil results for canine patients, and FIG. 23B showing earwax/cerumen results for canine patients.

As can be seen in FIG. 17A, the neutrophil score for treated dogs gradually decreased from the first to third treatments, and thereafter increased after the fourth treatment, which may indicate that the immune systems of the treated dogs had started to fight any bacterial and fungal infections related to the otitis condition. FIG. 23A presents the neutrophil score for all three Groups.

Figure 17B:
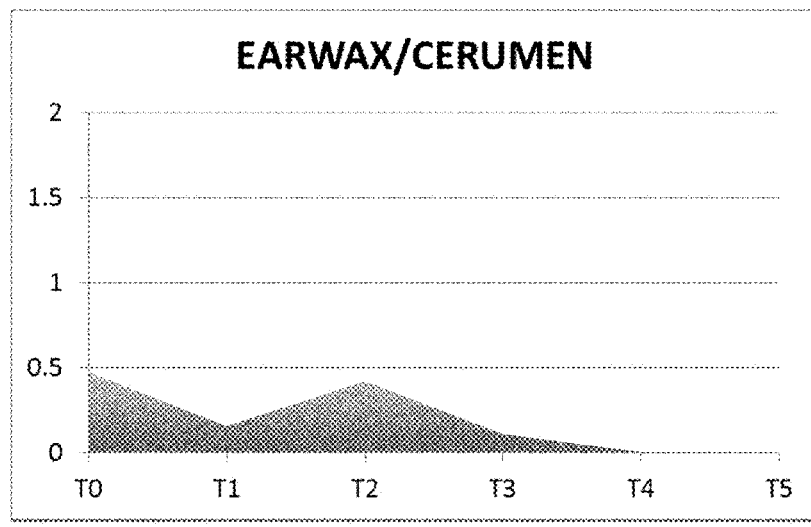
Figure 23B:
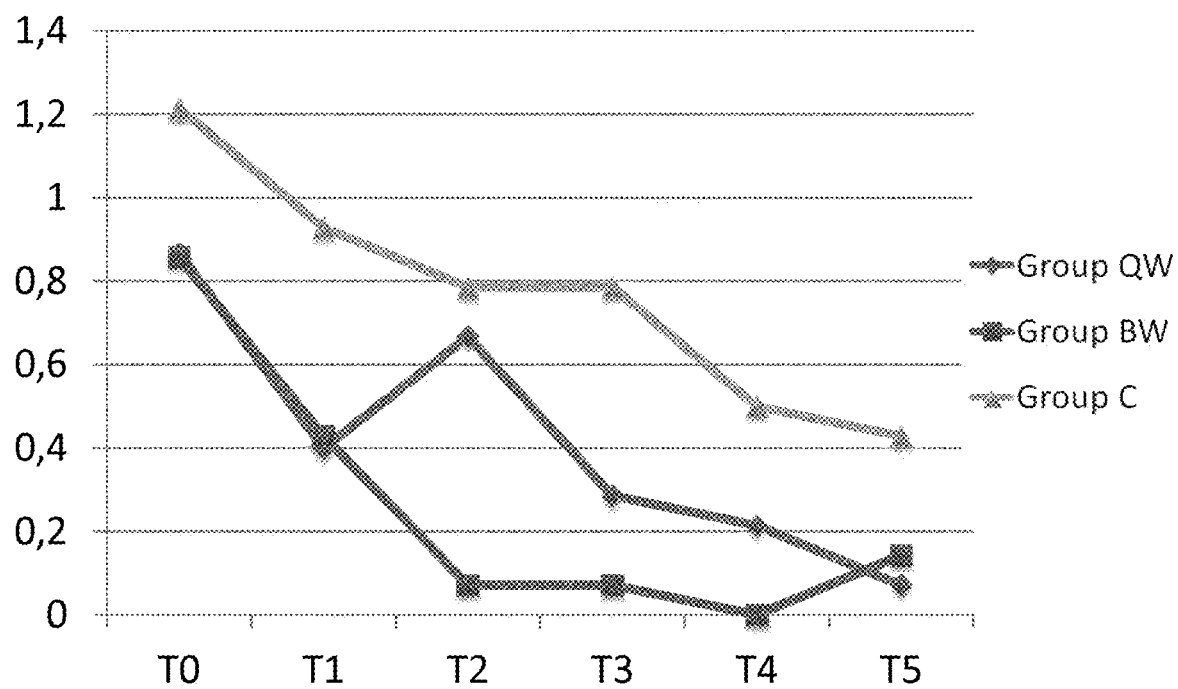

Regarding the presence of earwax/cerumen in the ear canals of the dogs that received the biophotonic composition treatment regimen, as shown in FIG. 17B, there was an increase in the presence of earwax following the first application of the biophotonic composition up to the second treatment, following which there was a pronounced decrease by the time that the third treatment was applied and thereafter an absence of cerumen from the otitis-afflicted ear canal of the canine patients, indicating a complete cleaning of the ear canals of cerumen. FIG. 23B presents the earwax/cerumen measurements in all three Groups. In FIG. 23B, there was an overall decrease in the presence of earwax for dogs treated with the biophotonic therapy. In both Group I (QW) and Group II (BW).

Figure 18A:
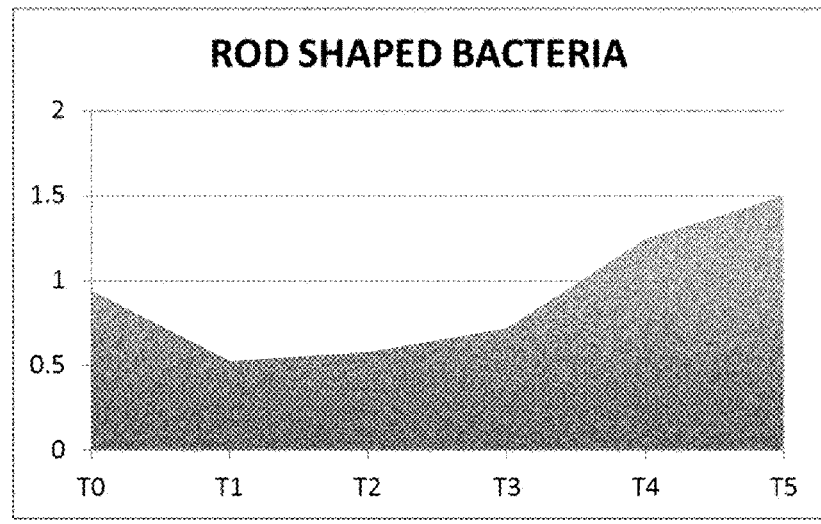
FIGS. 18A-18C presents graphs of further cytological assessment criteria, with FIG. 18A showing rod shaped bacteria results in the canine patient population receiving the biophotonic composition treatment, FIG. 18B showing the coccoid bacterial population results in the biophotonic composition treatment population, and FIG. 18C showing the malassezia population results in the biophotonic composition treatment patient population.
Figure 18B:
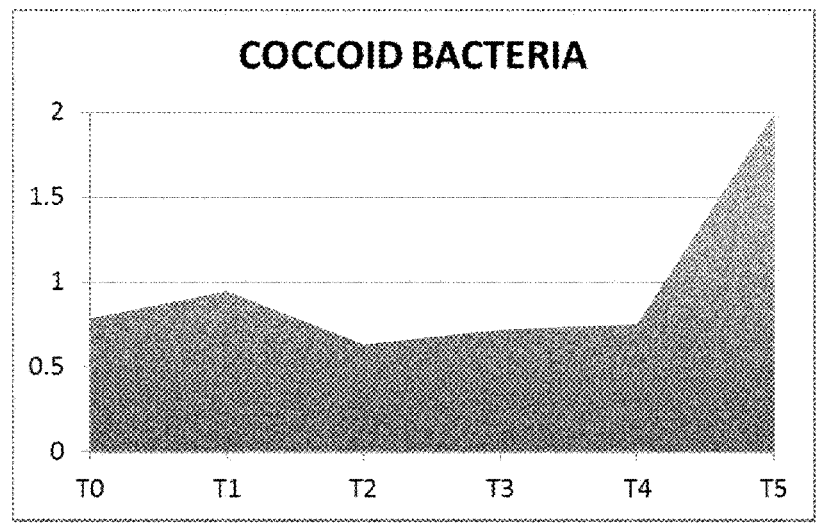
Figure 18C:
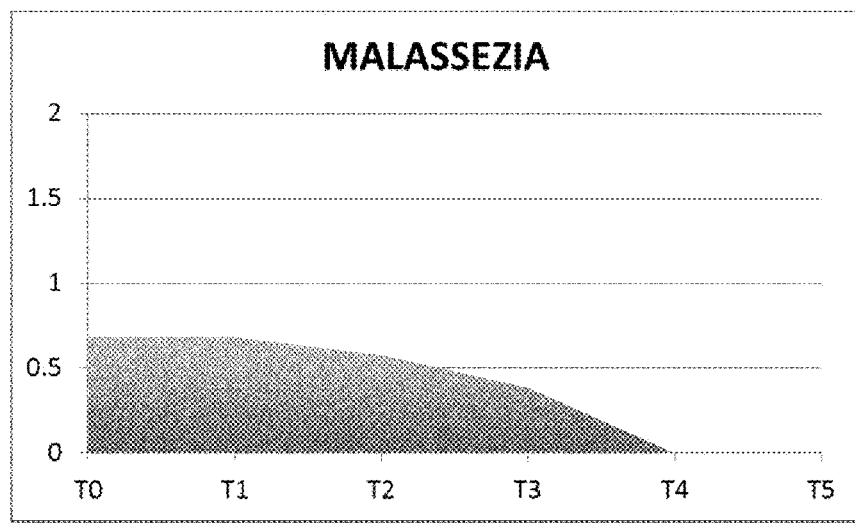
Figure 24A:
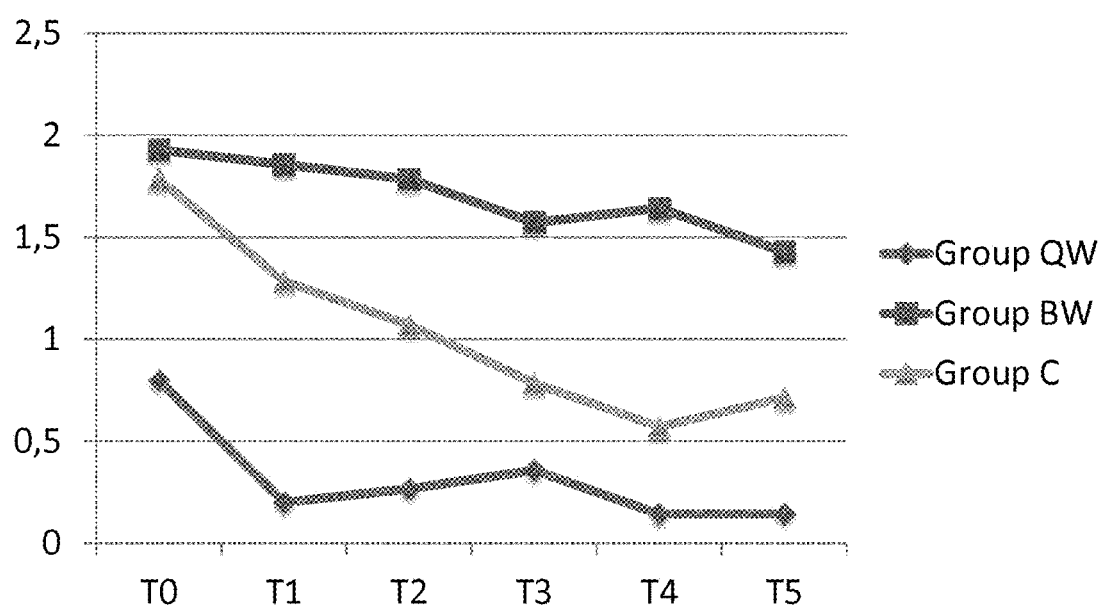
FIGS. 24A-24C present graphs of cytological assessment criteria, with FIG. 24A showing rod shaped bacteria results in the canine patient, FIG. 24B showing the coccoid bacterial population results in the canine patient, and FIG. 24C showing the malassezia population results in the canine patient.
Figure 24B:
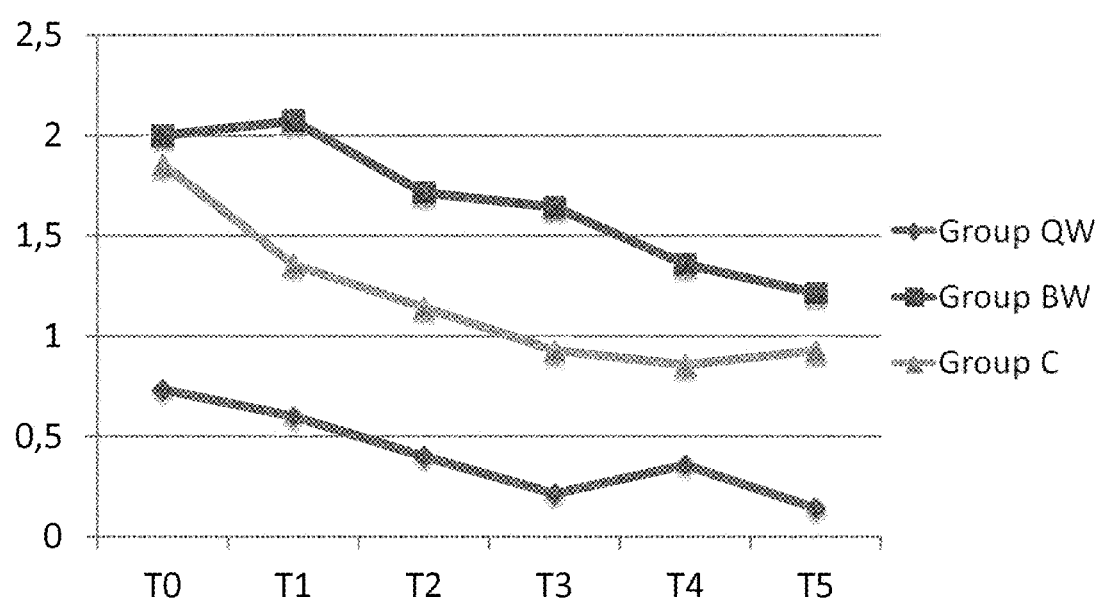
Figure 24C:
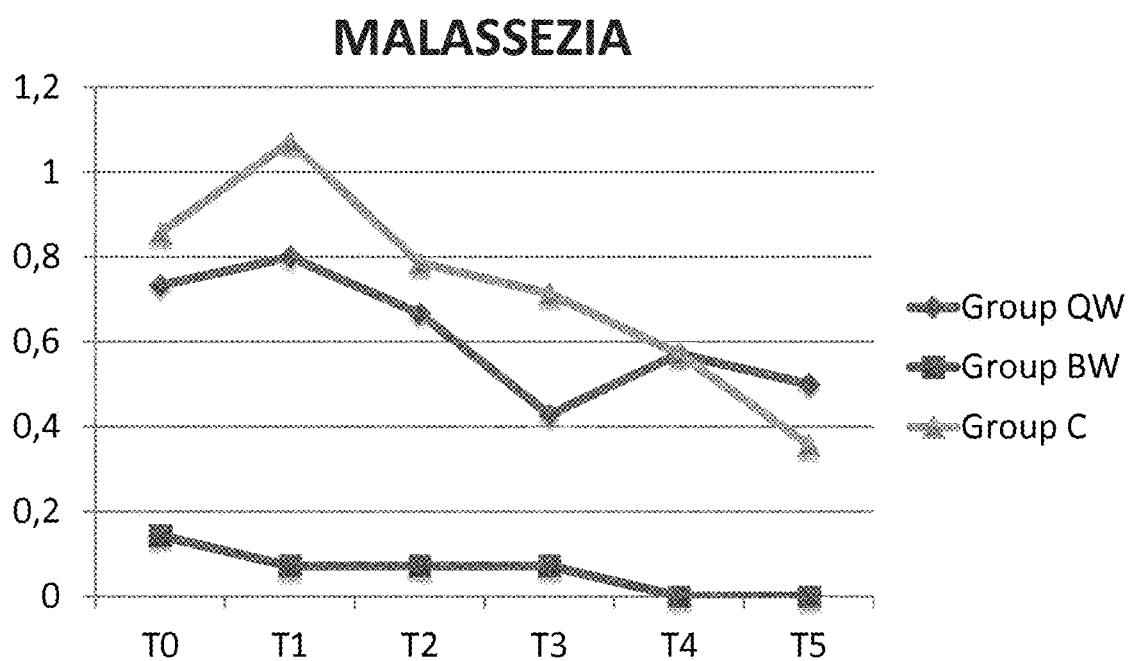

Bacterial populations were also evaluated as part of the cytological assessment criteria, and as can be seen from FIGS. 18A and 18B, the bacterial ecology present in the biophonic composition treated ear canals of the canine patients markedly shifted towards a greater presence of rod shaped bacteria (FIG. 18A) and coccoid bacteria after the third and fourth treatments, respectively. Yeast populations in the otitis-afflicted ear canals of the canine patients steadily decreased after the first treatment with the biophotonic compositions, to the point where by the fourth treatment; the presence of malassezia could not be detected (see FIG. 18C). FIGS. 24A and 24B present the bacterial ecology data for all three Groups. A decrease was observed for bacterial counts in canine patients for both the rod shaped bacteria and coccoid bacteria. FIG. 24C presents the yeast population comparison in all three Groups.

(3) Results According to Bacteriology

Figure 19A:
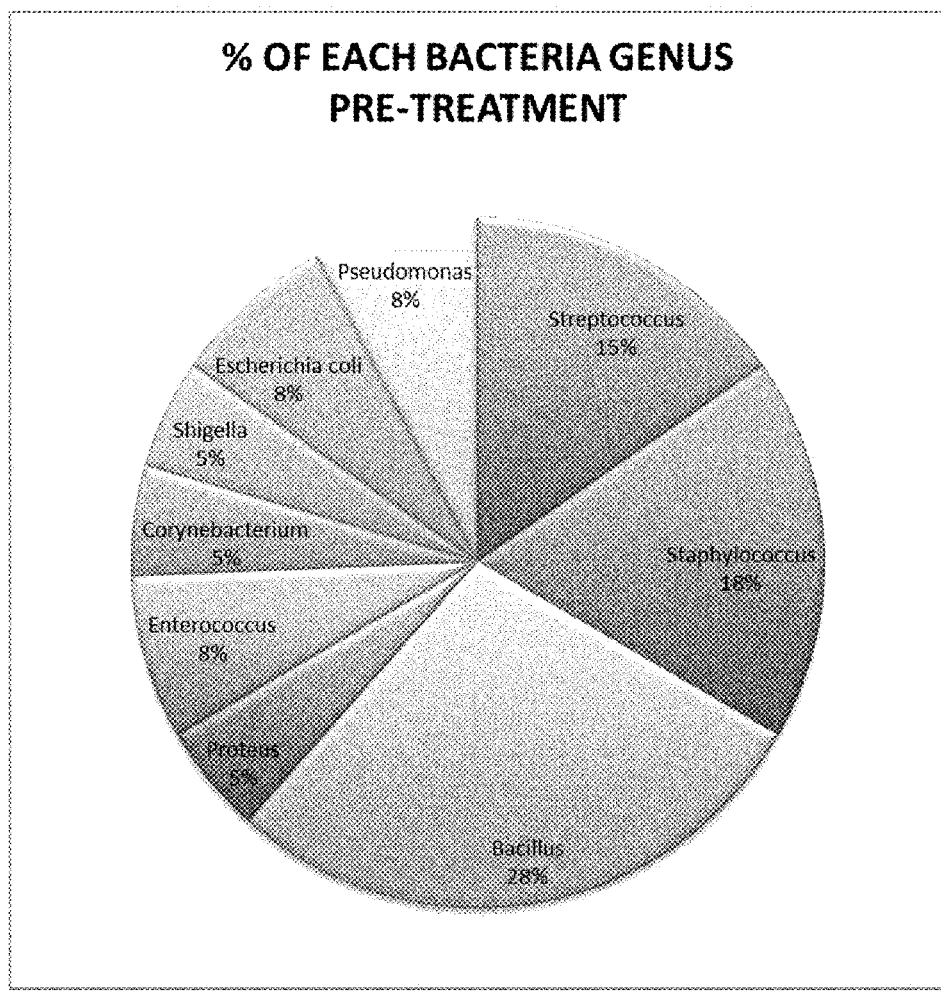
FIGS. 19A-19B present graphs of bacteriology assessment criteria, with FIG. 19A showing a pie chart of the bacterial species and genera in the otitis-afflicted ear canals in canine patients pre-treatment, and FIG. 19B showing a pie chart of the bacterial species and genera in the otitis-afflicted ear canals in canine patients post-treatment and during follow-up.
Figure 19B:
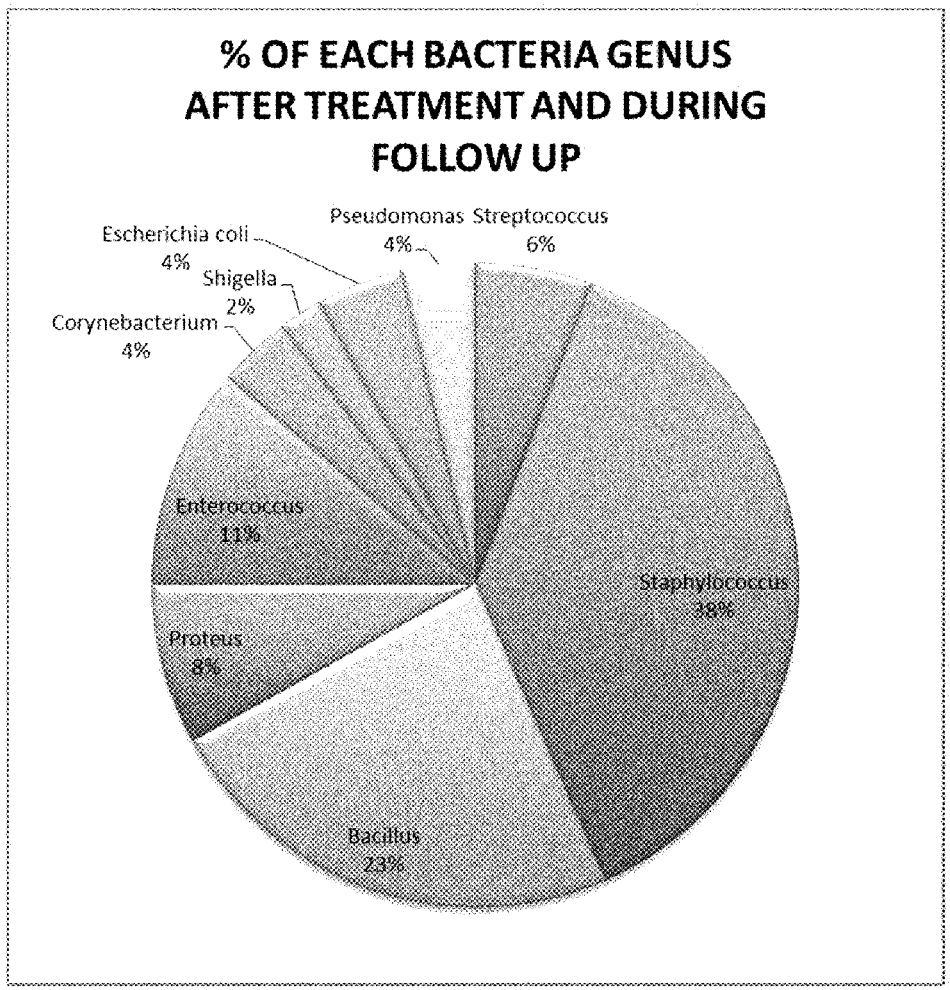
Figure 25A:
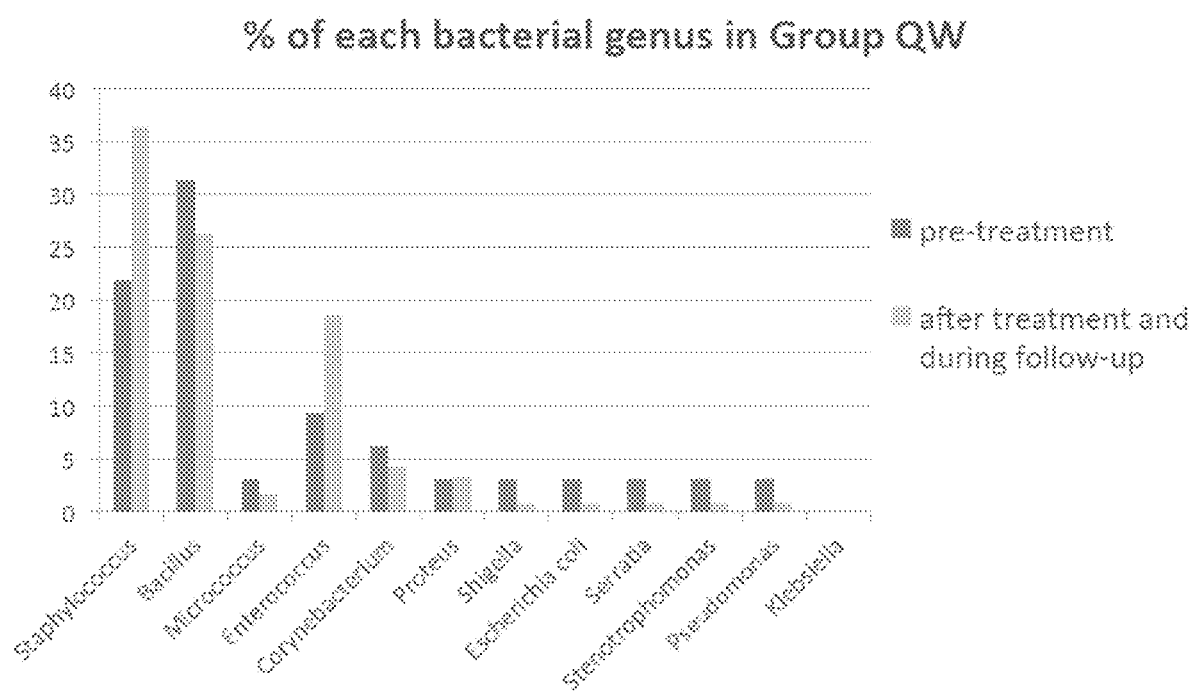
FIGS. 25A-25C present graphs of bacteriology assessment results.
Figure 25B:
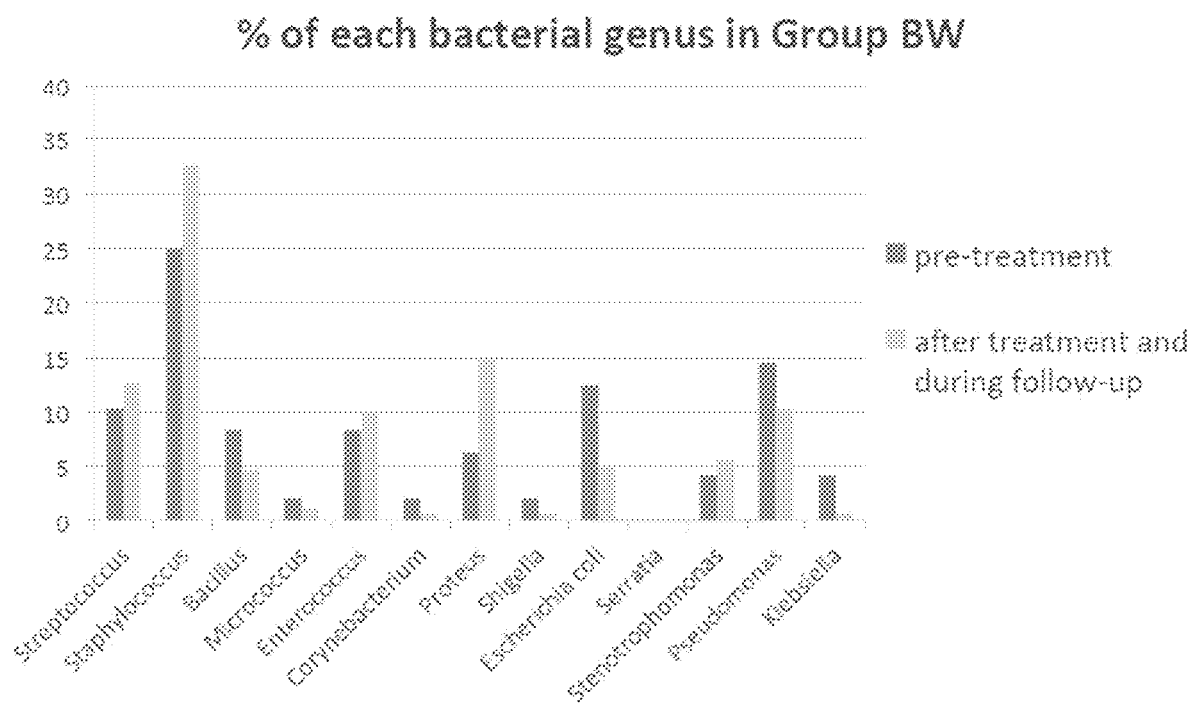
Figure 25C:
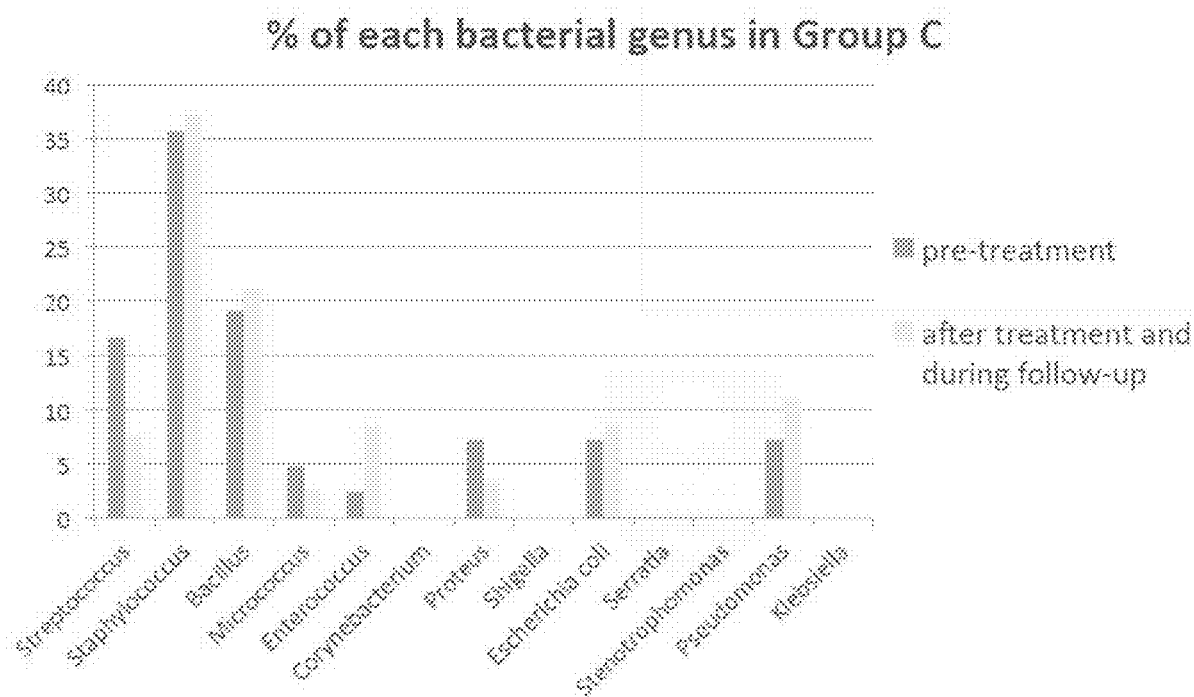

Otitis externa patients were also assessed pre-treatment and post-treatment for particular species or genera of bacteria populating the otitis-afflicted ear canals, and the pre-treatment results overall are presented in FIG. 19A while the post-treatment and follow-up results overall are presented in FIG. 19B. Regarding the pre-treatment results, it can be seen that nearly 40% of the overall bacterial flora in the otitis-afflicted patients comprised those types of bacterial species and genera that are associated with diseased or contaminated conditions, including *Streptococcus*, *Pseudomonas*, *Escherichia coli*, *Shigella* and *Corynebacterium*. For the post-treatment assessment, a shift in the bacterial flora populations was observed, with the relative amount of *Staphylococcus* population and the aforementioned bacterial species and genera greatly reduced and the overall number of colony forming units from swabs taken from the ear canals that had received the biophotonic composition treatment greatly reduced. FIGS. 25A-25C present the percentages of bacterial genera in all three Groups pre-treatment and after treatment/during follow-up.

While embodiments of the disclosure have been described above and illustrated in the accompanying figures, it will be evident to those skilled in the art that modifications may be made therein without departing from the essence of this disclosure. Such modifications are considered as possible variants comprised in the scope of the disclosure.

INCORPORATION BY REFERENCE

All references cited in this specification, and their references, are incorporated by reference herein in their entirety where appropriate for teachings of additional or alternative details, features, and/or technical background.

EQUIVALENTS

While the disclosure has been particularly shown and described with reference to particular embodiments, it will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

The invention claimed is:

1. A method of treating otitis extrena or chronic otitis extrena comprising
   a) applying a biophotonic composition to a patient in need thereof, wherein the biophotonic composition comprises at least one oxidant and at least one chromophore capable of activating the oxidant and
   b) exposing said biophotonic composition to actinic light for a time sufficient for said chromophore to cause activation of said oxidant.

2. The method according to claim 1, wherein the composition is applied to an auricle and/or ear canal of a patient.

3. The method according to claim 1, wherein said biophotonic composition is exposed to actinic light for a period of less than about 5 minutes.

4. The method according to claim 1, wherein said biophotonic composition is exposed to actinic light for a period of less than about 5 minutes per cm2 of an area to be treated.

5. The method according to claim 1, wherein said actinic light is visible light having a wavelength between about 400 nm and about 700 nm.

6. The method according to claim 1, wherein the oxidant is chosen from hydrogen peroxide, carbamide peroxide and benzoyl peroxide.

7. The method according to claim 1, wherein the oxidant is carbamide peroxide.

8. The method according to claim 1, wherein the oxidant is chosen from peroxy acid and an alkali metal percarbonate.

9. The method according to claim 1, wherein the oxidant is present in an amount of from about 1% to about 10% by weight of the total composition.

10. The method according to claim 1, wherein the composition further comprises at least one healing factor chosen from hyaluronic acid, glucosamine and allantoin.

11. The method according to claim 1, wherein the composition further comprises at least one gelling agent.

12. The method according to claim 11, wherein the gelling agent is chosen from glucose, modified starch, methyl cellulose, carboxymethyl cellulose, propyl cellulose, hydroxypropyl cellulose, a carbomer, alginic acid, sodium alginate, potassium alginate, ammonium alginate, calcium alginate, agar, carrageenan, locust bean gum, pectin, and gelatin.

13. The method according to claim 1, wherein the chromophore is chosen from a xanthene derivative dye, an azo dye, a biological stain, and a carotenoid.

14. The method according to claim 13, wherein said xanthene derivative dye is chosen from a fluorene dye, a fluorone dye, and a rhodole dye.

15. The method according to claim 14, wherein said fluorone dye is chosen from fluorescein and fluorescein derivatives.

16. The method according to claim 15, wherein said fluorescein derivative is chosen from phloxine B, rose bengal, and merbromine.

17. The method according to claim 15, wherein said fluorescein derivative is chosen from Eosin Y, Eosin B and Erythrosine B.

18. The method according to claim 17, wherein said fluorescein derivative is Eosin Y.

19. The method according to claim 1, wherein the patient is treated once a week for one or more weeks.

20. The method according to claim 1, wherein the patient is treated twice a week for one or more weeks.

* * * * *